(12) United States Patent
Furukawa et al.

(10) Patent No.: US 11,129,781 B2
(45) Date of Patent: *Sep. 28, 2021

(54) AGENT FOR HAIR DEFORMING TREATMENT

(71) Applicant: KAO CORPORATION, Tokyo (JP)

(72) Inventors: Junichi Furukawa, Tokyo (JP); Shinichi Tokunaga, Tokyo (JP); Masaru Tsuchiya, Saitama (JP)

(73) Assignee: KAO CORPORATION, Tokyo (JP)

( * ) Notice: Subject to any disclaimer, the term of this patent is extended or adjusted under 35 U.S.C. 154(b) by 903 days.

This patent is subject to a terminal disclaimer.

(21) Appl. No.: 15/532,967

(22) PCT Filed: Nov. 17, 2015

(86) PCT No.: PCT/JP2015/082282
§ 371 (c)(1),
(2) Date: Jun. 2, 2017

(87) PCT Pub. No.: WO2016/088549
PCT Pub. Date: Jun. 9, 2016

(65) Prior Publication Data
US 2018/0353406 A1    Dec. 13, 2018

(30) Foreign Application Priority Data
Dec. 5, 2014 (JP) .............. JP2014-247483

(51) Int. Cl.
*A61Q 5/04* (2006.01)
*A61K 8/365* (2006.01)
*A61K 8/34* (2006.01)
*A45D 7/06* (2006.01)

(52) U.S. Cl.
CPC .............. *A61K 8/365* (2013.01); *A45D 7/06* (2013.01); *A61K 8/34* (2013.01); *A61K 8/347* (2013.01); *A61Q 5/04* (2013.01); *A45D 2200/15* (2013.01)

(58) Field of Classification Search
None
See application file for complete search history.

(56) References Cited

U.S. PATENT DOCUMENTS

| | | | |
|---|---|---|---|
| 2,319,359 A | 5/1943 | Wassenegger | |
| 4,278,659 A | 7/1981 | Breuer | |
| 6,805,136 B2 * | 10/2004 | Browning | A45D 7/06 132/204 |
| 2006/0096042 A1 | 5/2006 | Schonert et al. | |
| 2008/0075682 A1 | 3/2008 | Cassier et al. | |
| 2008/0108732 A1 | 5/2008 | Wieland et al. | |
| 2010/0300472 A1 | 12/2010 | Malle et al. | |
| 2012/0312317 A1 | 12/2012 | Mannozzi | |
| 2013/0118520 A1 | 5/2013 | Mannozzi | |
| 2013/0298933 A1 * | 11/2013 | Malle | A61K 8/35 132/206 |
| 2015/0290096 A1 * | 10/2015 | Rose | A45D 7/06 132/206 |
| 2015/0305469 A1 * | 10/2015 | Paul | A61K 8/342 132/206 |

FOREIGN PATENT DOCUMENTS

| | | |
|---|---|---|
| CN | 101061151 A | 10/2007 |
| CN | 103002765 A | 3/2013 |
| EP | 1655056 B1 | 7/2008 |
| EP | 2 538 916 | 9/2011 |
| JP | 2005-194261 A | 7/2005 |
| JP | 2009-537619 A | 10/2009 |
| JP | 2013-520468 A | 6/2013 |
| JP | 2013-531046 A | 8/2013 |
| JP | 2016-47851 A | 4/2016 |
| JP | 2016-108320 A | 6/2016 |
| JP | 2016-108321 A | 6/2016 |
| JP | 2016-108322 A | 6/2016 |
| RU | 2012-140303 A | 3/2014 |
| WO | WO-2012/010351 A2 | 1/2012 |
| WO | WO-2014-067702 A1 | 5/2014 |
| WO | WO 2014/068101 A2 | 5/2014 |
| WO | WO-2014072645 A1 * | 5/2014 ............... A61Q 5/04 |

OTHER PUBLICATIONS

Boga et al., "Formaldehyde replacement with glyoxylic acid in semipermanent hair straightening: a new and multidisciplinary investigation", International Journal of Cosmetic Science, 36, pp. 459-470, Apr. 11, 2014.
International Search Report for International Patent Application No. PCT/JP2015/082282 dated Jan. 26, 2016.
Extended European Search Report dated Jun. 13, 2018 in corresponding application No. 15865038.2.
M. Wong, et al., "Mechanism of hair straightening", Journal of the Society Cosmetic Chemistry, Society of Cosmetic Chemists, US, vol. 45, Nov. 1, 1994, pp. 347-352.
P. M. Zarembski et al., "The Fluorimetric Microdetermination of Glyoxylic Acid in Blood, Urine and Bacterial Extracts", Biochem. J. 96.1(1965):218, pp. 219-220.

\* cited by examiner

Primary Examiner — Jyothsna A Venkat
(74) Attorney, Agent, or Firm — Foley & Lardner LLP

(57) ABSTRACT

An agent for hair deforming treatment comprising the following components (A), (B) and (C):
  (A) glyoxylic acid, or a hydrate or a salt thereof,
  (B) resorcin, and
  (C) water,
wherein the molar ratio of the content of the component (B) to the content of the component (A), (B)/(A), is 0.2 or more and 5 or less.

4 Claims, No Drawings

AGENT FOR HAIR DEFORMING TREATMENT

CROSS-REFERENCE TO RELATED APPLICATIONS

The present application is a U.S. national stage application of International Patent Application No. PCT/JP2015/082282, filed Nov. 17, 2015, which claims the benefit of priority to Japanese Patent Application No. 2014-247483, filed Dec. 5, 2014, the entireties of which are hereby incorporated by reference.

FIELD OF THE INVENTION

The present invention relates to an agent for hair deforming treatment capable of semi-permanently or permanently deforming the shape of hair.

BACKGROUND OF THE INVENTION

As methods for semi-permanently or permanently deforming the shape of hair, there have been a method of using a reducing agent, as in the case of the formation of a semi-permanent wave, and a method of using an agent for a strongly-alkaline treatment having a pH 12 to 14, including an alkali relaxer as a representative example. However, it has been well known that these methods impart a severe impact on hair, and damage the hair. In addition, in recent years, as a method for semi-permanently or permanently deforming the hair with less damage to the hair, a hair-relaxing method using a large amount of formaldehyde has been developed. However, such a method of using highly toxic formaldehyde must be handled carefully, because of its high volatility, and thus, the method is not always a preferred method of hair treatment.

Hence, a hair-relaxing method, which does not impart damage to hair and does not use formaldehyde, and which is safer to a human body, has been desired. For example, Patent Document 1 discloses a technology of applying α-keto acid, and particularly, glyoxylic acid to hair, and then subjecting the hair to a heat treatment with a flat iron at 200° C.±50° C., to convert very curly hair to straight hair. Moreover, Patent Document 2 discloses a method which comprises applying a polyhydroxylated aromatic compound to hair, and then heating the hair to a temperature of 110° C. or higher, to permanently relax keratin fibers.

Meanwhile, temporary hair deformation, such as the resetting of a hair style by rinsing the hair with water, can be realized by using a hair styling agent. For example, Patent Document 3 discloses a hair cosmetic composition, which is prepared by heating glyceraldehyde and resorcin to reflux in the presence of boric acid and silicic acid, to form an oligomer. Patent Document 3 describes that this composition improves set retentivity and humidity resistance, is capable of reforming the hair style by wetting the hair with water, and improves the mechanical strength of hair.
[Patent Document 1] EP 2538916 A
[Patent Document 2] JP-A-2009-537619
[Patent Document 3] U.S. Pat. No. 4,278,659 B

SUMMARY OF THE INVENTION

The present invention provides an agent for hair deforming treatment comprising the following components (A), (B) and (C):

(A) glyoxylic acid, or a hydrate or a salt thereof,
(B) resorcin, and
(C) water,
wherein the molar ratio of the content of the component (B) to the content of the component (A), (B)/(A), is 0.2 or more and 5 or less.

Moreover, the present invention provides a method of hair treatment for semi-permanently or permanently deforming the shape of hair, which comprises the following steps (i) and (ii):

(i) applying the above described agent for hair deforming treatment to hair, and then allowing the agent to penetrate into the hair, and (ii) heating and shaping the hair into which the agent for hair deforming treatment has penetrated.

DETAILED DESCRIPTION OF THE INVENTION

When the hair treatment agent used in the method described in Patent Document 1 or 2 is applied to hair, although it could convert the hair to straight hair semi-permanently, it could not provide a semi-permanently or permanently wavy or curly shape to the hair. In addition, when the once formed semi-permanent or permanent straight shape intends to be converted to another semi-permanent or permanent shape such as a wavy or curly shape, it is necessary to perform again a conventional operation of using a reducing agent. Thus, excessive amounts of time and efforts are required, and further, hair may be damaged.

Meanwhile, the technology described in Patent Document 3 is characterized in that it is washed away with water because an oligomer is used as a treatment agent. As such, the hair is returned to its original hair shape by being repeatedly washed, and thus, this technology cannot be considered to be semi-permanent or permanent hair deformation.

Accordingly, the present invention relates to an agent for hair deforming treatment and a method of hair treatment, which are safe for human bodies and have less damage to hair, are able to semi-permanently or permanently provide not only a shape of straight hair, but also a wavy or curly shape, and further, are able to easily convert the once formed hair style to another semi-permanent or permanent hair shape, without using an agent for hair deforming treatments based on such as a reducing agent, and without damaging the hair.

The present inventors have found that a hair treatment agent comprising glyoxylic acid and resorcin cannot only semi-permanently provide a straight hair shape or a curly or a wavy hair shape to hair, but also deform hair that has once been treated with this hair treatment agent, to any completely different, any hair shape, by only using a heating means such as a hair iron or a curler, without treating the hair with a hair treatment agent such as a reducing agent, thereby completing the present invention.

The agent for hair deforming treatment of the present invention is highly safe for human bodies, has less damage to hair, and can deform the shape of hair semi-permanently or permanently, and the hair deformed with the present agent for hair deforming treatment does not lose its effect even if the hair is for example washed with a shampoo. In addition, once the present agent for hair deforming treatment is applied to hair, it is not necessary to allow a hair treatment agent to penetrate into the hair again, and the hair can be repeatedly deformed semi-permanently or permanently only by heating to the hair. Moreover, the hair, which has been arbitrarily repeatedly deformed by being heated, still has a high hair washing resistance of the shape of the hair, and thus the shape of the hair does not lose it effect by contact with shampoo, water, etc.

In the present invention, "semi-permanent or permanent hair deformation" means that hair has extremely excellent hair washing resistance, and that the shape of the hair does not change, even if shampooing is repeatedly carried out thereon. Specifically, it means that, when the deformed hair is washed with shampoo, and the shampoo is then fully washed away with water, and the hair is then naturally dried, the shape of hair is maintained before and after shampooing. It is to be noted that the expression "the shape of hair is maintained" means that, for example, in the case of wavy hair, the number of waves is not substantially different before and after shampooing, and in the case of straight hair, wavy or curly hair is not substantially generated as a result of shampooing.

In the present invention, "hair deformation" means deformation of hair, which is not caused by the cleavage and recombination of the S—S bond of proteins in hair, and it includes deformation of straight hair into for example curly hair, and also, deformation of hair which has been deformed into wavy or curly hair, or naturally curly hair, to straight hair.

[Component (A): Glyoxylic Acid, or a Hydrate or a Salt Thereof]

The component (A) includes not only glyoxylic acid, but also a hydrate of the glyoxylic acid and a salt of the glyoxylic acid. An example of the hydrate of the glyoxylic acid is a glyoxylic acid monohydrate. Examples of the salt of the glyoxylic acid include an alkaline metal salt of the glyoxylic acid and an alkaline-earth metal salt of the glyoxylic acid. Examples of the alkaline metal salt include a lithium salt, a sodium salt, and a potassium salt. Examples of the alkaline-earth metal salt include a magnesium salt and a calcium salt.

From the viewpoint of achieving a more significant change in the shape of hair after the treatment of hair with the agent for hair deforming treatment of the present invention, achieving more excellent hair washing resistance of the shape of hair, achieving a more significant change in the shape of hair upon semi-permanent re-deformation of the shape of hair by heating, and also achieving more excellent hair washing resistance of the shape of hair after completion of the re-deformation, the content of the component (A) in the agent for hair deforming treatment of the present invention is, in terms of the content of glyoxylic acid, preferably 1 mass % or more, more preferably 2 mass % or more, even more preferably 2.5 mass % or more, and further preferably 3 mass % or more, and in addition to the aforementioned viewpoint, also from the viewpoint of suppression of irritation to the skin, the content of the component (A) is preferably 30 mass % or less, more preferably 25 mass % or less, even more preferably 20 mass % or less, even more preferably 15 mass % or less, and even more preferably 12 mass % or less.

[Component (B): Resorcin]

From the viewpoint of achieving a more significant change in the shape of hair after the treatment of hair with the agent for hair deforming treatment of the present invention, achieving more excellent hair washing resistance of the shape of hair, achieving a more significant change in the shape of hair upon semi-permanent re-deformation of the shape of hair by heating, and also achieving more excellent hair washing resistance of the shape of hair after completion of the re-deformation, the content of the component (B) in the agent for hair deforming treatment of the present invention is preferably 1 mass % or more, more preferably 2 mass % or more, even more preferably 3 mass % or more, further preferably 4 mass % or more, and still further preferably 5 mass % or more, and in addition to the aforementioned viewpoint, also from the viewpoint of suppression of irritation to the skin, the content of the component (B) is preferably 30 mass % or less, more preferably 25 mass % or less, even more preferably 20 mass % or less, and further preferably 17 mass % or less.

From the viewpoint of, because of a condensate of the component (A) and the component (B) formed in hair, achieving a more significant change in the shape of hair after the treatment of hair with the agent for hair deforming treatment of the present invention, achieving more excellent hair washing resistance of the shape of hair, achieving a more significant change in the shape of hair upon semi-permanent re-deformation of the shape of hair by heating, and also achieving more excellent hair washing resistance of the shape of hair after completion of the re-deformation, the molar ratio of the content of the component (B) to the content of the component (A) in the agent for hair deforming treatment of the present invention, (B)/(A), is 0.2 or more, preferably 0.3 or more, more preferably 0.4 or more, even more preferably 0.5 or more, and further preferably 0.7 or more, and it is 5 or less, preferably 2.5 or less, more preferably 2 or less, even more preferably 1.5 or less, and further preferably 1.2 or less.

[Component (C): Water]

The agent for hair deforming treatment of the present invention contains water as a medium. In addition to water, a lower alcohol containing from 1 to 3 carbon atoms, such as methanol or ethanol, can be used in combination with water, as necessary. In this case, the content of the lower alcohol containing from 1 to 3 carbon atoms in the agent for hair deforming treatment of the present invention is preferably 60 mass % or less, more preferably 40 mass % or less, even more preferably 30 masse or less, further preferably 20 mass % or less, still further preferably 15 mass % or less, and still further preferably 10 mass % or less. It is preferably 0.1 mass % or more.

[Component (D): A Compound Represented by Formula (1)]

Furthermore, in order to more easily change the shape of hair, the agent for hair deforming treatment of the present invention preferably comprises, as a component (D), a compound represented by the following formula (1):

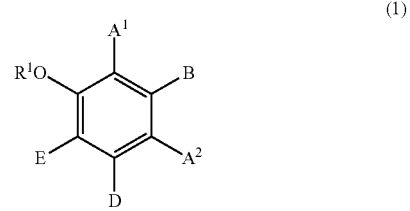

wherein $R^1$ represents a hydrogen atom or a methyl group, $A^1$ and $A^2$, which may be the same or different, each represents a hydrogen atom, a straight-chain or branched-chain alkyl group or alkenyl group containing from 1 to 12 carbon atoms, an optionally substituted aralkyl group or arylalkenyl group containing from 7 to 12 carbon atoms, a straight-chain or branched-chain alkoxy group or alkenyloxy group containing from 1 to 6 carbon atoms, a halogen atom, or —CO—R² (wherein R² represents a straight-chain or branched-chain alkyl group or alkenyl group containing from 1 to 12 carbon atoms, an optionally substituted aralkyl group or arylalkenyl group containing from 7 to 12 carbon atoms, or an optionally substituted aromatic hydrocarbon group containing from 6 to 12 carbon atoms), B represents a hydrogen atom, a straight-chain or branched-chain alkyl group or alkenyl group containing from 1 to 12 carbon atoms, an optionally substituted aralkyl group or arylalkenyl group containing from 7 to 12 carbon atoms, —OR³, or —COOR³ (wherein R³ represents a hydrogen atom, or a straight-chairs or branched-chain alkyl group or alkenyl group containing from 1 to 6 carbon atoms), D represents a hydrogen atom, a hydroxy group, a methyl group, or a straight-chain or branched-chain alkoxy group or alkenyloxy group containing from 1 to 12 carbon atoms, and E represents a hydrogen atom, a hydroxy group, a straight-chain or branched-chain alkyl group or alkenyl group containing from 1 to 6 carbon atoms, or a straight-chain or branched-chain alkoxy group or alkenyloxy group containing from 1 to 6 carbon atoms, provided that two or three of A¹, A², B and E are hydrogen atoms, and the remaining groups do not include sulfo groups, and that when D is a hydrogen atom or a methyl group, A¹ and B, or A² and B, together with two carbon atoms adjacent to them, form a benzene ring optionally substituted with a hydroxy group.

In the formula (1), when the aralkyl group, arylalkenyl group, or aromatic hydrocarbon group has a substituent, examples of the substituent include a hydroxy group, a straight-chain or branched-chain alkyl group or alkenyl group containing from 1 to 6 carbon atoms, and an alkoxy group containing from 1 to 12 carbon atoms. In addition, the number of carbon atoms contained in the aralkyl group, arylalkenyl group, or aromatic hydrocarbon group indicates the total number of carbon atoms including the number of carbon atoms contained in substituents.

Examples of the straight-chain or branched-chain alkyl group or alkenyl group containing from 1 to 6 carbon atoms, which is represented by R³, include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a 1-methylpentyl group, an n-hexyl group, an iso-hexyl group, a vinyl group, an allyl group, a butenyl group, a hexenyl group.

An example of the straight-chain or branched-chain alkoxy group or alkenyloxy group containing from 1 to 6 carbon atoms, which is represented by A¹, A² or E, is a group formed by binding an oxygen atom to the above described alkyl group or alkenyl group containing from 1 to 6 carbon atoms.

Examples of the straight-chain or branched-chain alkyl group or alkenyl group containing from 1 to 12 carbon atoms, which is represented by A¹, A², R² or B, include the above described alkyl group or alkenyl group containing from 1 to 6 carbon atoms, an n-heptyl group, a 2,4-dimethylpentyl group, a 1-n-propylbutyl group, an n-octyl group, a 2-ethylhexyl group, an n-nonyl group, a 1-methylnonyl group, an n-decyl group, a 3,7-dimethyloctyl group, a 2-isopropyl-5-methylhexyl group, an n-undecyl group, an n-dodecyl group, and a decenyl group.

An example of the straight-chain or branched-chain alkoxy group or alkenyloxy group containing from 1 to 12 carbon atoms, which is represented by D, is a group formed by binding an oxygen atom to the above described alkyl group or alkenyl group containing from 1 to 12 carbon atoms.

Examples of the optionally substituted aralkyl group or arylalkenyl group containing from 7 to 12 carbon atoms, which is represented by A¹, A², R² or B, include a benzyl group, a hydroxybenzyl group, a dihydroxybenzyl group, a phenylethyl group, a phenylethenyl group, a hydroxyphenylethyl group, a dihydroxyphenylethyl group, a hydroxyphenylethenyl group, a dihydroxyphenylethenyl group, a phenylpropyl group, a phenylpropenyl group, a 1-naphthylmethyl group, a 2-naphthylmethyl group, and a 1-indanyl group.

Examples of the optionally substituted aromatic hydrocarbon group containing from 6 to 12 carbon atoms, which is represented by R², include a phenyl group, a hydroxyphenyl group, a dihydroxyphenyl group, a trihydroxyphenyl group, a naphthyl group, a hydroxynaphthyl group, and a dihydroxynaphthyl group.

Examples of the halogen atom represented by A¹ or A² include a fluorine atom, a chlorine atom, and a bromine atom.

Specific examples of the compound represented by the formula (1) include a compound represented by the following formula (1-1), a benzophenone derivative represented by the following formula (1-2), and a naphthol derivative represented by the following formula (1-3-a) or (1-3-b):

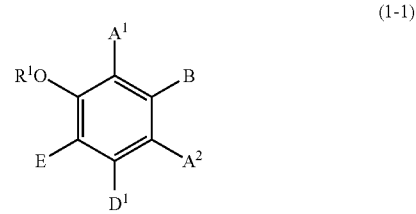

(1-1)

wherein R¹, A¹, A², B and E are as defined above, and D¹ represents a hydroxy group or a methoxy group,

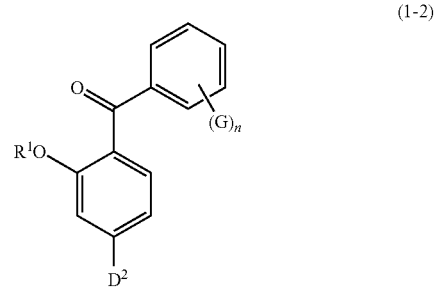

(1-2)

wherein R¹ is defined as that described above, D² represents a hydroxy group, or an alkoxy group containing from 1 to 12 carbon atoms, G represents a hydroxy group, a straight-chain or branched-chain alkyl group or alkenyl group containing from 1 to 6 carbon atoms, or an alkoxy group containing from 1 to 6 carbon atoms, and n represents an integer of from 0 to 2, and

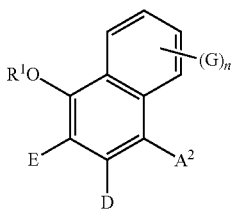

(1-3-a)

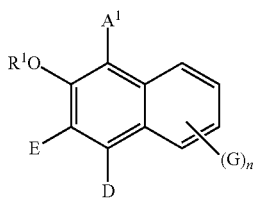

(1-3-b)

wherein $R^1$, $A^1$, E, D, G and n are as defined above.

Preferred examples of the compound represented by the formula (1-1) include the following compounds (1-1-1) to (1-1-3).

(1-1-1) An m-dimethoxybenzene derivative represented by the following formula (1-1-1):

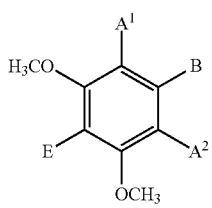

(1-1-1)

wherein $A^1$, $A^2$, B and E are as defined above.

$A^1$ and $A^2$ each represents, preferably a hydrogen atom, or a straight-chain or branched-chain alkyl group or alkenyl group containing from 1 to 4 carbon atoms, and more preferably a hydrogen atom.

B represents, preferably a hydrogen atom, an alkyl group or alkenyl group containing from 1 to 4 carbon atoms, an optionally substituted arylalkenyl group containing from 7 to 10 carbon atoms, or a hydroxy group, and more preferably a hydrogen atom, an optionally substituted arylalkenyl group containing from 7 to 10 carbon atoms, or a hydroxy group.

E represents, preferably a hydrogen atom, or a straight-chain or branched-chain alkyl group or alkenyl group containing from 1 to 4 carbon atoms, and more preferably a hydrogen atom.

Examples of the compound corresponding to (1-1-1) include 1,3-dimethoxybenzene, 3,5-dimethoxyphenol, 2,6-dimethoxyphenol, and 5-(hydroxyphenylethenyl)-1,3-dimethoxybenzene (trivial name: pterostilbene).

(1-1-2) An m-methoxyphenol derivative represented by the following formula (1-1-2):

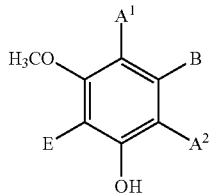

(1-1-2)

wherein $A^1$, $A^2$, B and E are as defined above.

$A^1$ and $A^2$ each represent, preferably a hydrogen atom, a straight-chain or branched-chain alkyl group or alkenyl group containing from 1 to 12 carbon atoms, or an optionally substituted aralkyl group or arylalkenyl group containing from 7 to 12 carbon atoms, and more preferably a hydrogen atom, a straight-chain or branched-chain alkyl group containing from 1 to 6 carbon atoms, or an optionally substituted arylalkenyl group containing from 7 to 10 carbon atoms.

B represents, preferably a hydrogen atom, a straight-chain or branched-chain alkyl group or alkenyl group containing from 1 to 12 carbon atoms, an optionally substituted aralkyl group or arylalkenyl group containing from 7 to 12 carbon atoms, or —$OR^3$ (wherein $R^3$ represents a hydrogen atom, or a straight-chain or branched-chain alkyl group or alkenyl group containing from 1 to 6 carbon atoms), more preferably a hydrogen atom, an alkyl group or alkenyl group containing from 1 to 4 carbon atoms, an optionally substituted arylalkenyl group containing from 7 to 10 carbon atoms, or a hydroxy group, and even more preferably a hydrogen atom, an optionally substituted arylalkenyl group containing from 7 to 10 carbon atoms, or a hydroxy group.

E represents, preferably a hydrogen atom, a hydroxy group, a straight-chain or branched-chain alkyl group or alkenyl group containing from 1 to 4 carbon atoms, or a straight-chain or branched-chain alkoxy group or alkenyloxy group containing from 1 to 4 carbon atoms, and more preferably a hydrogen atom or a hydroxy group.

Examples of the compound corresponding to (1-1-2) include 3-methoxyphenol, 5-methoxy resorcin, 3-methoxybenzene-1,2-diol, 4-butyl-3-methoxyphenol, 3-methoxy-4-(1-phenylethyl)phenol, and 5-(4-hydroxyphenylethenyl)-1-hydroxy-3-methoxybenzene (trivial name: Pinostilbene).

(1-1-3) A resorcin derivative represented by the following formula (1-1-3):

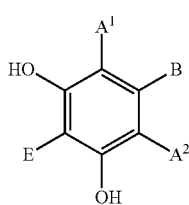

(1-1-3)

wherein $A^1$, $A^2$, B and E are as defined above.

Examples of the resorcin derivative include those represented by the following formulae (i) or (ii).

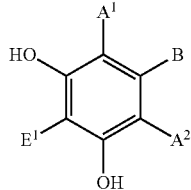

(i)

wherein $A^1$, $A^2$ and B are as defined above, $E^1$ represents a hydroxy group, a straight-chain or branched-chain alkyl group or alkenyl group containing from 1 to 6 carbon atoms, or a straight-chain or branched-chain alkoxy group or alkenyloxy group containing from 1 to 6 carbon atoms.

$A^1$ and $A^2$ each represent, preferably a hydrogen atom, or a straight-chain or branched-chain alkyl group or alkenyl group containing from 1 to 12 carbon atoms, and more preferably a hydrogen atom.

B represents, preferably a hydrogen atom, an optionally substituted aralkyl group or arylalkenyl group containing from 7 to 12 carbon atoms, —$OR^3$ (wherein $R^3$ represents a hydrogen atom, or a straight-chain or branched-chain alkyl group or alkenyl group containing from 1 to 4 carbon atoms).

$E^1$ preferably represents a hydroxy group, a straight-chain or branched-chain alkyl group or alkenyl group containing from 1 to 4 carbon atoms, or a straight-chain or branched-chain alkoxy group or alkenyloxy group containing from 1 to 4 carbon atoms.

Examples of the resorcin derivative represented by the formula (i) include:

2-alkyl resorcin, such as 2-methyl resorcin, 2-ethyl resorcin, or 2-propyl resorcin;

pyrogallol;

2-alkoxy resorcin, such as 2-methoxy resorcin;

gallic acid, and gallic acid ester, such as methyl gallate, ethyl gallate, propyl gallate, or butyl gallate; and 5-(phenylethenyl) 2-isopropyl resorcin.

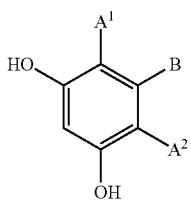

(ii)

wherein $A^1$, $A^2$, B and E are as defined above.

The resorcin derivative represented by the formula (ii) is more preferably a resorcin derivative represented by the following formula (ii-1) or (ii-2).

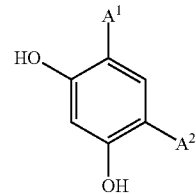

(ii-1)

wherein $A^1$ and $A^2$ are as defined above.

Examples of the resorcin derivative represented by the formula (ii-1) include:

4-alkyl resorcin, such as 4-methyl resorcin, 4-ethyl resorcin, 4-propyl resorcin, 4-isopropyl resorcin, 4-butyl resorcin (trivial name: Rucinol), 4-isobutyl resorcin, 4-sec-butyl resorcin, 4-tert-butyl resorcin, 4-pentyl resorcin, 4-isopentyl resorcin, 4-sec-pentyl resorcin, 4-tert-pentyl resorcin, 4-neopentyl resorcin, 4-hexyl resorcin, 4-isohexyl resorcin, 4-heptyl resorcin, 4-octyl resorcin, 4-(2-ethylhexyl) resorcin, 4-nonyl resorcin, 4-decyl resorcin, 4-undecyl resorcin, or 4-dodecyl resorcin;

4-alkenyl resorcin, such as 4-vinyl resorcin, 4-allyl resorcin, 4-butenyl resorcin, 4-hexenyl resorcin, or 4-decenyl resorcin;

4-aralkyl resorcin, such as 4-benzyl resorcin, 4-(1-phenylethyl) resorcin (trivial name: Symwhite 377), 4-(2-phenylethyl) resorcin, or 4-(3-phenylpropyl) resorcin;

4-hydroxyaralkyl resorcin, such as 4-(4-hydroxybenzyl) resorcin, 4-(2,4-dihydroxybenzyl) resorcin, 4-(4-hydroxyphenylethyl) resorcin, or 4-(2,4-dihydroxyphenylethyl) resorcin;

4-arylalkenyl resorcin, such as 4-(1-phenylethenyl) resorcin or 4-(3-phenylpropenyl) resorcin;

4-hydroxyarylalkenyl resorcin, such as 4-(4-hydroxyphenylethenyl) resorcin or 4-(2,4-dihydroxyphenylethenyl) resorcin;

4-(1-methylnaphthyl) resorcin;

4-alkoxy resorcin, such as 4-methoxy resorcin, 4-ethoxy resorcin, 4-isopropoxy resorcin, 4-propoxy resorcin, 4-butoxy resorcin, 4-sec-butoxy resorcin, 4-tert-butoxy resorcin, or 4-pentoxy resorcin;

halogenated resorcin, such as 4-chloro resorcin or 4-bromo resorcin;

4-alkanoyl resorcin, such as 4-acetyl resorcin, 4-propanoyl resorcin, 4-butanoyl resorcin, 4-pentanoyl resorcin, or 4-hexanoyl resorcin; and 4-arylalkanoyl resorcin, such as 4-phenylethanoyl resorcin, 4-phenylpropanoyl resorcin, 4-phenylbutanoyl resorcin, 4-phenylpentanoyl resorcin, 4-phenylhexanoyl resorcin, or 3-(hydroxyphenyl)-1-(2,4-dihydroxyphenyl)propen-1-one (trivial name: Isoliquiritigenin).

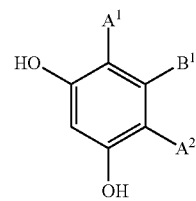

(ii-2)

wherein $A^1$ and $A^2$ are as defined above, and $B^1$ represents a straight-chain or branched-chain alkyl group or alkenyl group containing from 1 to 12 carbon atoms, an optionally substituted aralkyl group or arylalkenyl group containing from 7 to 12 carbon atoms, —OR$^3$, or —COOR$^3$ (wherein R$^3$ represents a hydrogen atom, or a straight-chain or branched-chain alkyl group or alkenyl group containing from 1 to 6 carbon atoms).

The resorcin derivative represented by the formula (ii-2) is more preferably a resorcin derivative represented by the following formula (ii-2-a) or (ii-2-b).

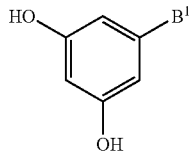

(ii-2-a)

wherein B$^1$ is defined as that described above.

Examples of the resorcin derivative represented by the formula (ii-2-a) include:

5-alkyl resorcin, such as 5-methyl resorcin, 5-ethyl resorcin, 5-propyl resorcin, 5-isopropyl resorcin, 5-butyl resorcin, 5-isobutyl resorcin, 5-sec-butyl resorcin, 5-tert-butyl resorcin, 5-pentyl-resorcin (trivial name: Olivetol), 5-isopentyl resorcin, 5-neopentyl resorcin, 5-hexyl resorcin, 5-isohexyl resorcin, 5-heptyl resorcin, 5-octyl resorcin, 5-(2-ethylhexyl) resorcin, 5-nonyl resorcin, 5-decyl resorcin, 5-undecyl resorcin, or 5-dodecyl resorcin;

5-alkenyl resorcin, such as 5-vinyl resorcin, 5-allyl resorcin, 5-butenyl resorcin, 5-hexenyl resorcin, or 5-decenyl resorcin;

phloroglucinol;

5-alkoxybenzene-1,3-diol, such as 5-ethoxybenzene-1,3-diol, 5-propoxybenzene-1,3-diol, or 5-butoxybenzene-1,3-diol;

3,5-dihydroxybenzoic acid;

3,5-dihydroxybenzoic acid ester, such as methyl 3,5-dihydroxybenzoate, ethyl 3,5-dihydroxybenzoate, propyl 3,5-dihydroxybenzoate, butyl 3,5-dihydroxybenzoate, pentyl 3,5-dihydroxybenzoate, or hexyl 3,5-dihydroxybenzoate;

5-aralkyl resorcin, such as 5-benzyl resorcin, 5-(1-phenylethyl) resorcin, 5-(2-phenylethyl) resorcin, or 5-(phenylpropyl) resorcin;

5-hydroxyaralkyl resorcin, such as 5-(4-hydroxybenzyl) resorcin, 5-(2,4-dihydroxybenzyl) resorcin, 5-(hydroxyphenylethyl) resorcin (trivial name: Dihydro-resveratrol), or 5-(2,4-dihydroxyphenylethyl) resorcin;

5-arylalkenyl resorcin, such as 5-(phenylethenyl) resorcin (trivial name: Pinosylvin) or 5-(phenylpropenyl) resorcin; and 5-hydroxyarylalkenyl resorcin, such as 5-(4-hydroxyphenylethenyl) resorcin (trivial name: Resveratrol), 5-(4-methoxyphenylethenyl) resorcin (trivial name: 4-MethoxyResveratrol), 5-(2,4-dihydroxyphenylethenyl) resorcin (trivial name: Oxyresveratrol), 5-(2-methoxy-4-hydroxyphenylethenyl) resorcin (trivial name: Gnetucleistol D), 5-(3,4-dimethoxyphenylethenyl) resorcin (trivial name: Gnetucleistol E), 5-(3-hydroxy-4-methoxyphenylethenyl) resorcin (trivial name: Rhapontigenin), 5-(4-hydroxy-3-methoxyphenylethenyl) resorcin (trivial name: Isorhapontigenin), or 5-(dihydroxyphenylethenyl) resorcin (trivial name: Piceatannol).

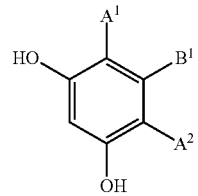

(ii-2-b)

wherein A$^1$, A$^2$ and B$^1$ are as defined above.

A$^1$ and A$^2$ each preferably represent a hydrogen atom, a straight-chain or branched-chain alkyl group or alkenyl group containing from 1 to 4 carbon atoms, or an alkoxy group or alkenyloxy group containing from 1 to 4 carbon atoms.

Examples of the resorcin derivative represented by the formula (ii-2-b) include:

2-alkylbenzene-1,3,5-triol, such as 2-methylbenzene-1,3,5-triol, 2-ethylbenzene-1,3,5-triol, 2-propylbenzene-1,3,5-triol, 2-butylbenzene-1,3,5-triol, 2-hexylbenzene-1,3,5-triol, 2-octylbenzene-1,3,5-triol, or 2-dodecylbenzene-1,3,5-triol;

2-aralkyl-1,3,5-triol, such as 2-benzylbenzene-1,3,5-triol, 2-(phenylethyl)benzene-1,3,5-triol, or 2-(phenylpropyl)benzene-1,3,5-triol;

phloroglucin acid ester, such as 2-acetylbenzene-1,3,5-triol, 2-propanoylbenzene-1,3,5-triol, 2-butanoylbenzene-1,3,5-triol, 2-phenylethanoylbenzene-1,3,5-triol, 2-hydroxyphenyl-1-(benzene-2,4,6-triol)ethan-1-one, 3-hydroxyphenyl-1-(benzene-2,4,6-triol)propan-1-one (trivial name: Phloretin), 4-hydroxyphenyl-1-(benzene-2,4,6-triol)butan-1-one, 2-benzoylbenzene-1,3,5-triol, 2-(hydroxybenzoyl)benzene-1,3,5-triol, 2-(3,5-dihydroxybenzoyl)benzene-1,3,5-triol, or 2-(2,4-dihydroxybenzoyl)benzene-1,3,5-triol; and 3,5-dihydroxybenzoic acid ester, such as 3,5-dihydroxy-2-methylbenzoic acid, methyl 3,5-dihydroxy-2-methylbenzoate, 3,5-dihydroxy-2-ethylbenzoic acid, methyl 3,5-dihydroxy-2-ethylbenzoate, 3,5-dihydroxy-2-propylbenzoic acid, methyl 3,5-dihydroxy-2-propylbenzoate, 3,5-dihydroxy-2-butylbenzoic acid, or methyl 3,5-dihydroxy-2-butylbenzoate.

Examples of the benzophenone derivative represented by the formula (1-2) include 4-benzoyl resorcin (trivial name: Benzophenone-1), 4-(hydroxybenzoyl) resorcin, 4-(dihydroxybenzoyl) resorcin, 4-(2,4-dihydroxybenzoyl) resorcin (trivial name: Benzophenone-2), 4-(methylbenzoyl) resorcin, 4-(ethylbenzoyl) resorcin, 4-(dimethylbenzoyl) resorcin, 4-(diethylbenzoyl) resorcin, 4-naphthoyl resorcin, 2-hydroxy-4-methoxybenzophenone (trivial name: Benzophenone-3), 2,2'-dihydroxy-4,4'-dimethoxybenzophenone (trivial name: Benzophenone-6), 2,2'-dihydroxy-4-methoxybenzophenone (trivial name: Benzophenone-8), 2-hydroxy-4-methoxy-4'-methylbenzophenone (trivial name: Benzophenone-10), and 2-hydroxy-4-octyloxybenzophenone (trivial name: Benzophenone-12).

The naphthol derivative represented by the formula (1-3-a) or (1-3-b) is preferably a naphthol derivative, wherein, in the formula (1-3-a) or (1-3-b), R$^1$ represents a hydrogen atom, or an alkyl group or alkenyl containing from 1 to 4 carbon atoms, and more preferably, a naphthol derivative, wherein, in the formula (1-3-a) or (1-3-b), R$^1$ represents a hydrogen atom.

Moreover, a naphthol derivative, wherein A$^1$ and A$^2$ each represent a hydrogen atom, a hydroxy group, a straight-chain or branched-chain alkyl group containing from 1 to 4 carbon atoms, or an alkoxy group containing from 1 to 4 carbon atoms, is preferable; and a naphthol derivative, wherein $A^1$ and $A^2$ each represent a hydrogen atom or a hydroxy group, is more preferable.

Furthermore, a naphthol derivative, wherein D represents a hydrogen atom, a hydroxy group, a straight-chain or branched-chain alkyl group containing from 1 to 4 carbon atoms, or an alkoxy group containing from 1 to 4 carbon atoms, is preferable.

Further, a naphthol derivative, wherein E represents a hydrogen atom, a hydroxy group, or an alkyl group containing from 1 to 4 carbon atoms or an alkoxy group containing from 1 to 4 carbon atoms, is preferable.

Examples of such a compound include 1-naphthol, 2-naphthol, 3-methylnaphthalen-1-ol, naphthalene-1,4-diol, naphthalene-1,5-diol, and naphthalene-1,8-diol.

Among the compounds represented by the formula (1), the m-dimethoxybenzene derivative represented by the formula (1-1-1), the resorcin derivative represented by the formula (1-1-3), the benzophenone derivative represented by the formula (1-2), and the naphthol derivative represented by the formula (1-3-a) or (1-3-b) are preferable. Moreover, 2-methyl resorcin, 4-chloro resorcin, 4-alkyl resorcin, 4-aralkyl resorcin, 4-acylated resorcin, 5-alkyl resorcin, 5-aralkyl resorcin, 5-hydroxyarylalkenyl resorcin, phloroglucin acid ester, gallic acid, and gallic acid ester are preferable. Furthermore, 4-butyl resorcin (trivial name: Rucinol), 4-(1-phenylethyl) resorcin (trivial name: Symwhite 377), 5-(hydroxyphenylethenyl) resorcin (trivial name: resveratrol), 3-hydroxyphenyl-1-(benzene-2,4,6-triol)propan-1-one (trivial name: Phloretin), 4-(2,4-dihydroxybenzoyl) resorcin (trivial name: Benzophenone-2), 5-(hydroxyphenylethenyl)-1,3-dimethoxybenzene (trivial name: Pterostilbene), and 1-naphthol are preferable. Further, 4-butyl resorcin, 4-(1-phenylethyl) resorcin, and 4-n-hexyl resorcin are preferable.

The molecular weight of the compound represented by the formula (1) is preferably 120 or more, and also, from the viewpoint of permeability into hair, it is preferably 1000 or less, more preferably 500 or less, and even more preferably 300 or less.

The component (D) can be used alone or in combination of two or more components. The use of two or more components is more preferable.

From the viewpoint of achieving a more significant change in the shape of hair after the treatment of hair with the agent for hair deforming treatment of the present invention, achieving more excellent hair washing resistance of the shape of hair, achieving a more significant change in the shape of hair upon semi-permanent re-deformation of the shape of hair by heating, and also achieving more excellent hair washing resistance of the shape of hair after completion of the re-deformation, when the agent for hair deforming treatment of the present invention comprises the component (D), the total content of the component (B) and the component (D) is preferably 5 mass % or more, more preferably 10 mass % or more, and even more preferably 15 mass % or more, and also, it is preferably 30 mass % or less, more preferably 27 mass % or less, even more preferably 25 mass % or less, and further preferably 23 mass % or less.

From the viewpoint of obtaining high effects, the mass ratio of the content of the component (D) to the content of the component (B), (D)/(B), is preferably 0.1 or more, more preferably 0.15 or more, and even more preferably 0.2 or more, and also, from the viewpoint of preventing eduction of the component (D) having low solubility after penetration of the agent into hair, leading to insufficient penetration of the agent into tissues in the hair, the mass ratio (D)/(B) is preferably 3 or less, more preferably 2 or less, even more preferably 1 or less, and further preferably 0.4 or less.

Moreover, from the viewpoint of further improving the effect of semi-permanently or permanently deforming hair and the effect of repeatedly, semi-permanently or permanently deforming hair only by heating, the molar ratio of the total content of the components (B) and (D) to the content of the component (A) in the agent for hair deforming treatment of the present invention, [(B)+(D)]/(A), is preferably 0.2 or more, more preferably 0.3 or more, even more preferably 0.4 or more, further preferably 0.5 or more, and still further preferably 0.7 or more, and also, it is preferably 5 or less, more preferably 2.5 or less, even more preferably 2 or less, further preferably 1.5 or less, and still further preferably 1.2 or less.

The agent for hair deforming treatment of the present invention may be either one-part agent, or a multi-part agent such as a two-part agent. From the viewpoint of ameliorating the permeability of the component (A) and the component (B) into hair and increasing the effects of the present invention, a multi-part agent comprising the component (A) and the component (B) in respective parts, and further, a two-part agent is more preferable. In the case of such a multi-part agent, a part comprising the component (A) is defined as a first agent and a part comprising the component (B) is defined as a second agent in the present invention.

In the case of the multi-part agent, the content of the component (A) in the first agent is, in terms of the content of glyoxylic acid, preferably 1 mass % or more, more preferably 2 mass % or more, even more preferably 2.5 mass % or more, and further preferably 3 mass % or more, and also, it is preferably 30 mass % or less, more preferably 25 mass % or less, even more preferably 20 mass % or less, further preferably 15 mass % or less, and still further preferably 12 mass % or less.

In the case of the multi-part agent, the content of the component (B) in the second agent is preferably 1 mass % or more, more preferably 2 mass % or more, even more preferably 3 mass % or more, further preferably 4 mass % or more, and still further preferably 5 mass % or more, and also, it is preferably 30 mass % or less, more preferably 25 mass % or less, even more preferably 20 mass % or less, and further preferably 17 mass % or less.

When the first agent and the second agent (and the other) are mixed in the multi-part agent and the obtained mixture is then used, the mixing ratio is not particularly limited. It is preferable that the composition obtained after the mixing of the parts become the agent for hair deforming treatment of the present invention. Accordingly, in the case of the multi-part agent, the contents of individual components are the contents thereof in the composition obtained after the mixing of the parts, unless otherwise specified. In addition, upon production of the multi-part agent, the multi-part agent can comprise the component (C) as a solvent for each part, and in a case where a two-part agent is produced, the component (C) is preferably present both in the part comprising the component (A) and in the part comprising the component (B). Moreover, when the multi-part agent comprises the component (D), the multi-part agent preferably comprises the component (B) and the component (D) in a single part, and thus, it is preferable to produce a multi-part agent, or further, a two-part agent, which comprises a first agent comprising the component (A) and a second agent comprising the component (B) and the component (D).

When the present agent for hair deforming treatment comprises the component (D), the mass ratio of the content of the component (D) to the content of the component (B) in the second agent, (D)/(B), is preferably 0.1 or more, more preferably 0.15 or more, and even more preferably 0.2 or more, and also, it is preferably 3 or less, more preferably 2 or less, even more preferably 1 or less, and further preferably 0.4 or less.

From the viewpoint of the permeability of the component (A) into hair, the pH of the agent for hair deforming treatment of the present invention is preferably 4 or less, more preferably 3 or less, even more preferably 2.5 or less, and further preferably 2 or less. In addition, from the viewpoint of suppression of hair damage and suppression of irritation to the skin, the pH of the present agent for hair deforming treatment is preferably 1 or more, more preferably 1.2 or more, and even more preferably 1.5 or more. In the case of the multi-part agent, the pH of the part comprising the component (A), namely, the pH of the first agent is preferably set in the above described range, and more preferably, the pH of the mixture obtained after mixing all of the parts is set in the above described range. In the present invention, the pH of the hair treatment agent indicates a value obtained by directly measuring the pH of the agent for hair deforming treatment at a room temperature (25° C.) using a pH meter, without for example dilution of the agent for hair deforming treatment.

In order to adjust the pH of the agent for hair deforming treatment to be in the above described range, a pH adjuster can be used, as appropriate. Examples of the pH adjuster as an alkali agent that can be used include: ammonia or a salt thereof; alkanolamine such as monoethanolamine, isopropanolamine, 2-amino-2-methylpropanol or 2-aminobutanol, or a salt thereof; alkanediamine such as 1,3-propanediamine, or a salt thereof; carbonates such as guanidine carbonate, sodium carbonate, potassium carbonate, sodium hydrogen carbonate, or potassium hydrogen carbonate; and hydroxides such as sodium hydroxide or potassium hydroxide. Moreover, as an acid agent, inorganic acids such as hydrochloric acid or phosphoric acid, hydrochlorides such as monoethanolamine hydrochloride, phosphates such as monopotassium dihydrogen phosphate or disodium monohydrogen phosphate, or organic acids other than the component (A), such as lactic acid or malic acid, can be used.

From the viewpoint of improving the touch feeling of hair after completion of a hair treatment and further improving the effects of the present invention, the agent for hair deforming treatment of the present invention preferably comprises a cationic surfactant. The cationic surfactant is preferably a mono-long-chain-alkyl quaternary ammonium salt having an alkyl group containing from 8 to 24 carbon atoms and three alkyl groups containing from 1 to 4 carbon atoms.

Preferably, at least one mono-long-chain-alkyl quaternary ammonium surfactant is selected from the group consisting of compounds represented by the following formula:

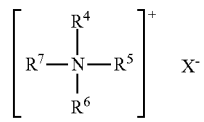

wherein $R^4$ represents a saturated or unsaturated, straight-chain or branched-chain alkyl group containing from 8 to 22 carbon atoms, $R^8$—CO—NH—$(CH_2)_m$—, or $R^8$—CO—O—$(CH_2)_m$— (wherein $R^8$ represents a saturated or unsaturated, straight-chain or branched-chain alkyl chain containing from 7 to 21 carbon atoms, and m represents an integer of from 1 to 4); $R^5$, $R^6$ and $R^7$ each independently represent an alkyl group containing from 1 to 4 carbon atoms or a hydroxylalkyl group containing from 1 to 4 carbon atoms, and $X^-$ represents a chloride ion, a bromide ion, a methosulfate ion, or an ethosulfate ion.

Examples of a preferred cationic surfactant include long-chain quaternary ammonium compounds such as cetyltrimethylammonium chloride, myristyltrimethylammonium chloride, behentrimonium chloride, cetyltrimethylammonium bromide, and stearamidopropyl trimonium chloride. These compounds can be used alone, or can also be used in the form of a mixture thereof.

The content of the cationic surfactant in the agent for hair deforming treatment of the present invention is preferably 0.05 mass % or more, and more preferably 0.1 mass % or more, and also, it is preferably 10 mass % or less, and more preferably 5 mass % or less. When the agent for hair deforming treatment is a multi-part agent, the multi-part agent may comprise the cationic surfactant in the first agent, or in the second agent, or both of the first and second agents.

Furthermore, from the viewpoint of improving the touch feeling of hair after completion of a hair treatment and achieving good manageability, the agent for hair deforming treatment of the present invention preferably comprises silicone. As such silicone, dimethylpolysiloxane and amino-modified silicone are preferable.

As dimethylpolysiloxane, either a cyclic or non-cyclic dimethylpolysiloxane polymer can be used. Examples include SH200 series, BY22-019, BY22-020, BY11-026, B22-029, BY22-034, BY22-050A, BY22-055, BY22-060, BY22-083 and FZ-4188 (all of which are manufactured by Dow Corning Toray Co., Ltd.), and KF-9088, KM-900 series, MK-15H and MK-88 (all of which are manufactured by Shin-Etsu Chemical Co., Ltd.).

As amino-modified silicone, all silicones having an amino group or an ammonium group can be used. Examples include amino-modified silicone oil, all or a part of terminal hydroxy groups of which are terminated with for example methyl groups, and amodimethicone, the terminus of which is not terminated. As preferred amino-modified silicone, a compound represented by the following formula can be used, for example:

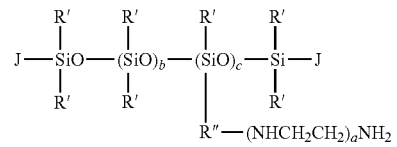

wherein R' represents a hydrogen atom, a hydroxy group, or $R^X$, wherein $R^X$ represents a substituted or unsubstituted monovalent hydrocarbon group containing from 1 to 20 carbon atoms; J represents $R^X$, R"—$(NHCH_2CH_2)_aNH_2$, $OR^X$, or a hydroxy group, wherein R" represents a divalent hydrocarbon group containing from 1 to 8 carbon atoms; a represents a number of from 0 to 3; and b and c each represent a number, in which the sum thereof is, at a number average, 10 or more and less than 20000, preferably 20 or more and less than 3000, more preferably 30 or more and less than 1000, and even more preferably 40 or more and less than 800.

Specific examples of a commercially available product of preferred amino-modified silicone include: amino-modified silicone oils such as SF8452C and SS3551 (both of which are manufactured by Dow Corning Toray Co., Ltd.), and KF-8004, KF-867S and KF-8015 (all of which are manufactured by Shin-Etsu Chemical Co., Ltd.); and amodimethicone emulsions such as SM8704C, SM8904, BY22-079, FZ-4671 and FZ4672 (all of which are manufactured by Dow Corning Toray Co., Ltd.).

The content of the silicone in the agent for hair deforming treatment of the present invention is preferably 0.1 mass % or more, more preferably 0.2 mass % or more, and even more preferably 0.5 mass % or more, and also, it is preferably 20 mass % or less, more preferably 10 mass % or less, and even more preferably 5 mass % or less. When the agent for hair deforming treatment is a multi-part agent, the multi-part agent may comprise the silicone in the first agent or in the second agent, or both of the first and second agents.

Further, from the viewpoint of improving the touch feeling of hair after completion of a hair treatment, the agent for hair deforming treatment of the present invention preferably comprises a cationic polymer.

The cationic polymer means a polymer having a cationic group or a group ionizable to such a cationic group. An amphoteric polymer, which can be cationic as a whole, is also included in the cationic polymer. That is to say, examples of the cationic polymer include water-soluble cationic polymers, which comprise an amino group or an ammonium group in the side chains thereof, or which comprise, as constitutional unit, a diallyl quaternary ammonium salt, such as a cationized cellulose derivative, cationic starch, a cationized guar gum derivative, a polymer or copolymer of diallyl quaternary ammonium salts, and a quaternary polyvinyl pyrrolidone derivative. In terms of effects such as touch feeling softness, smoothness, and easy to run fingers through hair obtained during rinsing or shampooing, manageability and moisture retention during drying, and the stability of the agent, among the aforementioned cationic polymers, a polymer comprising, as a constitutional unit, a diallyl quaternary ammonium salt, a quaternary polyvinyl pyrrolidone derivative, and a cationized cellulose derivative are preferable; and a polymer or copolymer of diallyl quaternary ammonium salts, and a cationized cellulose derivative are more preferable.

Specific examples of a preferred polymer or copolymer of diallyl quaternary ammonium salts include a dimethyldiallyl ammonium chloride polymer (Polyquaternium-6, for example, Marquardt 100; Lubrizol Advanced Materials), a dimethyldiallyl ammonium chloride/acrylic acid copolymer (Polyquaternium-22, for example, Marquardt 280 and Marquardt 295; Lubrizol Advanced Materials), and a dimethyldiallyl ammonium chloride/acrylamide copolymer (Polyquaternium-7, for example, Marquardt 550; Lubrizol Advanced Materials).

Specific examples of a preferred quaternary polyvinyl pyrrolidone derivative include polymers obtained by polymerizing a vinyl pyrrolidone copolymer with dimethylaminoethyl methacrylate (Polyquaternium-11, for example, GAFQUAT 734, GAFQUAT 755, and GAFQUAT 755N (all of which are manufactured by Ashland).

Specific examples of a preferred cationized cellulose include: polymers obtained by adding glycidyltrimethyl ammonium chloride to hydroxycellulose (Polyquaternium-10, for example, Leoguard G and Leoguard GP (both of which are manufactured by Lion Corporation); and Polymer JR-125, Polymer JR-400, Polymer JR-30M, Polymer LR-400, and Polymer LR-30M (all of which are manufactured by Amerchol Corp.)); and hydroxyethyl cellulose dimethyldiallyl ammonium chloride (Polyquaternium-4, for example, CELLCOAT H-100 and CELLCOAT L-200 (both of which are manufactured by Akzo Nobel)).

The content of the cationic polymer in the agent for hair deforming treatment of the present invention is preferably 0.001 mass % or more, more preferably 0.01 mass % or more, and even more preferably 0.05 mass % or more, and also, it is preferably 20 mass % or less, and more preferably 10 mass % or less. When the agent for hair deforming treatment is a multi-part agent, the multi-part agent may comprise the cationic polymer in the first agent, or in the second agent, or both of the first and second agents.

Further, the agent for hair deforming treatment of the present invention may also comprise an antioxidant in an amount ordinarily comprised in such an agent. The antioxidant may be an antioxidant generally used in the field of hair cosmetics, and an example of the antioxidant is ascorbic acid.

The agent for hair deforming treatment of the present invention may comprise, as appropriate, components generally mixed into hair cosmetics, as well as the aforementioned components. However, preferably, the agent for hair deforming treatment of the present invention substantially does not comprise a precursor, which is used in an oxidative hair color for coloring hair by an oxidation reaction between a precursor and a coupler. Specifically, the agent for hair deforming treatment of the present invention substantially does not comprise an aromatic compound having at least one amino group, having another amino group or a hydroxy group at the ortho position or para position of the one amino group, and also having a closed-shell quinoid structure when oxidized. The resorcin as a component (B) is a representative compound as a coupler used in an oxidative hair color. The present invention is characterized in that the component (A) is polymerized with the component (B) in hair, so that it makes possible to freely deform the shape of hair by the subsequent heating, and thus, the present invention is a technology completely different from the use of resorcin in an oxidative hair color.

In addition, the agent for hair deforming treatment of the present invention is also different from the technology disclosed in Patent Document 3, in which an oligomer of glyceraldehyde and resorcin is formed using boric acid or silicic acid, and thus, preferably, the agent for hair deforming treatment of the present invention substantially comprises neither boric acid nor silicic acid.

Moreover, preferably, the agent for hair deforming treatment of the present invention substantially does not comprise a hair reducing agent. The present invention is characterized in that it makes possible to deform hair, not depending on the cleavage of the S—S bond of proteins in hair. Thus, the present invention is a technology completely different from a permanent wave agent for deforming hair by cleaving the S—S bond of proteins in hair, using a reducing agent. Examples of the hair reducing agent include thioglycolic acid, dithioglycolic acid, cysteine, acetylcysteine, thiol such as butyrolactonethiol, hydrogen sulfite, and a salt thereof.

In the present invention, the expression "substantially does not comprise" is used to mean that the content of a target compound in the agent for hair deforming treatment is preferably less than 0.1 mass %, more preferably less than 0.01 mass %, and even more preferably, it means that the agent for hair deforming treatment does not comprise a target compound.

Since the agent for hair deforming treatment of the present invention is highly safe to human bodies and has less damage to hair, it can be preferably used particularly for human hair.

[Method of Hair Deforming Treatment]

A hair treatment for semi-permanently or permanently deforming the shape of hair using the agent for hair deforming treatment of the present invention can be carried out by a method of hair treatment comprising the following steps (i) and (ii):

(i) applying the agent for hair deforming treatment of the present invention to hair, and then allowing the agent to penetrate into the hair, and (ii) heating and shaping the hair into which the agent for hair deforming treatment has penetrated.

In the step (i), the agent for hair deforming treatment may be applied to dry hair or may also be applied to wet hair. In order to swell hair and to promote penetration of the hair treatment agent into the hair, hair is preferably wetted with water before the step (i). The mass of the agent for hair deforming treatment applied to hair in the step (i) is, at a bath ratio to the mass of the hair (the mass of the agent for hair deforming treatment/the mass of the hair), preferably 0.05 or more, more preferably 0.1 or more, even more preferably 0.25 or more, and further preferably 0.5 or more, and also, it is preferably 5 or less, more preferably 3 or less, and even more preferably 2 or less. The hair to be treated with the agent for hair deforming treatment may be either the entire hair or a part thereof.

In the step (i), the agent for hair deforming treatment can be applied to hair by any given method. In addition, when the agent for hair deforming treatment is a multi-part agent, the first agent comprising the component (A) may be mixed with the second agent comprising the component (B), and the obtained mixture may be then applied to hair. Otherwise, one of the first agent and the second agent may be applied to hair, and the other part may be then applied onto the portion applied. In a case where one part is applied onto the other part successively, from the viewpoint of promoting penetration of the agent for hair deforming treatment into hair and enhancing the effects, after one part had been applied to hair, the hair, to which the hair treatment agent has been applied, may be left, and thereafter, the other part may be applied onto the previously applied part. In such a case, in order to allow the agent for hair deforming treatment to penetrate and diffuse into hair, the standing time is preferably 1 minute or more, more preferably 3 minutes or more, and even more preferably 5 minutes or more, and also, it is preferably 1 hour or less, more preferably 30 minutes or less, and even more preferably 20 minutes or less. At this time, from the viewpoint of promoting penetration of the agent for hair deforming treatment into hair, heating may be carried out. When such heating is carried out, the heating is preferably carried out at a temperature of from 40° C. to 90° C. Moreover, when the two parts are successively applied to hair, the order of applying the parts is not particularly limited. From the viewpoint of promoting penetration of the agent for hair deforming treatment into hair and enhancing the effects, it is more preferable that the first agent be applied to hair, after the second agent has been applied thereto.

Furthermore, when the two parts are successively applied to hair, the amounts of the first agent and the second agent applied are not particularly limited. The two parts are applied, such that the molar ratio of the amount of the component (B) in the second agent applied to hair to the amount of the component (A) in the first agent applied to hair, (B)/(A), can be preferably 0.3 or more, more preferably 0.4 or more, and even more preferably 0.5 or more, and also, it can be preferably 5 or less, more preferably 2.5 or less, even more preferably 2 or less, and further preferably 1.5 or less. Specifically, for example, the ratio of the amount of the component (A) applied to hair, which is calculated from the content of the component (A) in the first agent and the amount of the first agent applied onto the hair, and the amount of the component (B) applied to hair, which is calculated from the content of the component (B) in the second agent and the amount of the second agent applied onto the hair, may be within the aforementioned range at a molar ratio.

When the second agent further comprises the component (D), the molar ratio of the total content of the components (B) and (D) in the second agent to the amount of the component (A) in the first agent applied to hair, [(B)+(D)]/(A), is preferably 0.2 or more, more preferably 0.3 or more, even more preferably 0.4 or more, further preferably 0.5 or more, and still further preferably 0.7 or more, and also, it is preferably 5 or less, more preferably 2.5 or less, even more preferably 2 or less, further preferably 1.5 or less, and still further preferably 1.2 or less.

A step of leaving hair, to which the hair treatment agent has been applied, may be inserted between the step (i) and the step (ii). In such a case, in order to allow the agent for hair deforming treatment to penetrate and diffuse into hair, the standing time is preferably 1 minute or more, more preferably 3 minutes or more, and even more preferably 5 minutes or more, and also, it is preferably 2 hours or less, more preferably 1 hour or less, even more preferably 30 minutes or less, and further preferably 20 minutes or less.

Moreover, from the viewpoint of promoting penetration of the agent for hair deforming treatment into hair, in the step of leaving hair, the hair may be heated. When the hair is heated, it is preferable to heat it at a temperature of from 40° C. to 90° C. By this heating operation, since a low-order oligomer can be produced in hair before the step (ii), heating is preferable, also in that the step (ii) can be carried out more advantageously.

Hair may be rinsed or may not be rinsed between the step (i) and the step (ii). From the viewpoint of sufficiently retaining the components of the hair treatment agent in hair, giving a semi-permanent shape to the hair, and further enhancing the effect of semi-permanently deforming the shape of the hair again by heating, it is preferable not to rinse the hair.

In order to increase interaction between the components (A) and (B) and hair proteins in hair, and also in order to promote a condensation reaction between the component (A) and the component (B) in hair to obtain the effects of the present invention, the heating temperature in the step (ii) is preferably 50° C. or higher, more preferably 60° C. or higher, and even more preferably 80° C. or higher, and also, in order to suppress rapid evaporation of water during heating, the heating temperature is preferably 250° C. or lower, more preferably 240° C. or lower, and even more preferably 230° C. or lower. Examples of the heating method include methods using a hair iron, an electric rod, a hot curler, etc.

The heating time applied in the step (ii) is selected, as appropriate, depending on the heating device and/or the heating temperature used. From the viewpoint of allowing the agent for hair deforming treatment to penetrate and diffuse into hair and to promote sufficient polymerization, the heating time is preferably 5 seconds or more, more preferably 1 minute or more, even more preferably 5 minutes or more, further preferably 15 minutes or more, and still further preferably 30 minutes or more, and also, in order to suppress hair damage, it is preferably 2 hours or less, more preferably 1 hour or less, and even more preferably 45 minutes or less.

Imparting a hair shape in the step (ii) includes both the imparting a straight shape and the imparting a curly shape. Examples of the method of giving a straight shape to hair include a method of blow-drying hair while pulling the hair with a hand, or with a tool such as a comb or a brush, and a method of heating hair using a hair iron. From the viewpoint of the ease of deformation, the method of using a hair iron is preferable. In order to provide a straight shape to hair, while heating the hair using a hair iron, a method of holding hair with a flat iron and then moving the flat iron from the roots to the tips, or a method of holding hair with a flat iron and then retaining the shape, while pulling the hair with a hand, or a tool such as a comb or a brush, may be applied. Otherwise, a combination of the two above methods may also be applied. When a curly shape is to be provided to hair, for example, a method of curling hair with an electric heating rod, a hot curler, etc., and then retaining the shape, while heating the hair, a method of winding hair around a curl iron and then retaining the shape are applied.

The step (ii) is preferably carried out in an environment in which rapid evaporation of water is suppressed. Examples of a specific means for suppressing evaporation of water include a method of covering hair, to which the hair treatment agent has been applied, with a plastic film such as plastic film for food products, a cap, etc., and a method of continuously spraying water vapor such as superheated vapor to hair.

After completion of the step (ii), hair may be rinsed, or may not be rinsed. From the viewpoint of preventing reduction in hair touch feeling due to excess polymers, the hair is preferably rinsed.

It is considered that, by these treatments, the components (A) and (B) penetrate into hair, and thereby, an interaction of these components with hair proteins occurs. In addition, in the hair, a thermoplastic condensate of the components (A) and (B) is generated. Thus, the shape of hair can be easily deformed by heating hair, and further, once the treatment is performed, hair can be freely and repeatedly deformed, semi-permanently or permanently, only by heating the hair, without applying the hair treatment agent again. Moreover, the hair deformation provided by the method of the present invention is not lost even by washing it with shampoo or the like, and it can be maintained for a long period of time.

(Re-Deforming Treatment Method)

After hair has been subjected to deforming treatment by a method comprising the step (i) or the step (ii), a step of semi-permanently re-deforming the hair to another shape by heating it can be carried out. When hair is re-deformed, it is preferable to heat the hair at a temperature of preferably 30° C. or higher, and more preferably 40° C. or higher, and also, at a temperature of preferably 230° C. or lower, more preferably 220° C. or lower, and even more preferably 210° C. or lower. In addition, when hair is subjected to re-deforming treatment, it is preferable not to apply any one of the agent for hair deforming treatment of the present invention, a hair treatment agent comprising a reducing agent, such as, what is called, a permanent wave agent, and known agent for hair deforming treatments such as an alkaline relaxer.

Hereafter, specific procedures for carrying out a step of semi-permanently re-deforming hair to another shape by heating will be described.

Case of re-deforming hair subjected to deforming treatment into curly shape into a straight shape In order to re-deform hair, which has been once subjected to deforming treatment into a curly shape, into a straight shape, for example, a method of blow-drying hair with a dryer, while pulling the hair with a hand, or a tool such as a comb or a brush, a method of heating hair with a hair iron are applied. From the viewpoint of the ease of deformation, the method of using the hair iron is preferable. In order to provide a straight shape to hair, while heating the hair with a hair iron, a method of holding hair with a hair iron and then moving the hair iron from the roots to the tips, or a method of holding hair with a hair iron and then retaining the shape, while pulling the hair with a hand, or a tool such as a comb or a brush, may be applied. Otherwise, a combination of the two above methods may also be applied.

In this case, from the viewpoint of deforming the shape of hair semi-permanently or permanently, regardless of the type of a hair iron used, the material of a heating portion, a preset temperature, and the operational method of a hair iron, the attained temperature during the heating of hair (the temperature of hair) is preferably 120° C. or higher, and more preferably 150° C. or higher, and also, from the viewpoint of achieving both prevention of hair damage and semi-permanent or permanent deformation of the shape of hair, the attained temperature is preferably 230° C. or lower, more preferably 220° C. or lower, and even more preferably 210° C. or lower. The temperature at which hair is heated can be measured, for example, using a radiation thermometer (Model No.: ST653) manufactured by SENTRY.

Case of re-deforming hair subjected to deforming treatment into a straight shape into curly shape In order to re-deform hair, which has been once subjected to deforming treatment into a straight shape, into a curly shape, for example, a method of curling hair with a rod, a curler, etc., and then retaining the shape, while heating the hair, or a method of winding hair around a hair iron and then retaining the shape are applied.

In this case, from the viewpoint of deforming the shape of hair semi-permanently or permanently, the attained temperature during the heating of hair (the temperature of hair) is preferably 30° C. or higher, and more preferably 40° C. or higher, and also, from the viewpoint of achieving both prevention of hair damage and semi-permanent or permanent deformation of the shape of hair, the attained temperature is preferably 180° C. or lower, more preferably 120° C. or lower, even more preferably 100° C. or lower, further preferably 80° C. or lower, and still further preferably 60° C. or lower.

Even in a case where hair is re-deformed, upon heating it, either a method of heating hair, which is dried, or a method of heating hair after wetting it with water, may be applied. From the viewpoint of semi-permanently or permanently deforming the shape of hair, the method of heating hair after wetting it with water is preferable.

The heating time applied when hair is re-deformed is selected, as appropriate, depending on the heating temperature. From the viewpoint of semi-permanently or permanently deforming the shape of hair, the heating time is preferably 1 second or more, more preferably 5 seconds or more, even more preferably 1 minute or more, further more preferably 5 minutes or more, still further preferably 15 minutes or more, and still further preferably 30 minutes or more. In addition, in order to suppress hair damage, it is preferably 2 hours or less, more preferably 1 hour or less, and even more preferably 45 minutes or less.

Since the method of hair treatment of the present invention is a technology capable of freely changing hair based on a principle, which is completely different from a permanent wave treatment using a reducing agent or a relaxer treatment using a strongly-alkaline hair treatment agent having pH 12 to 14, the present method does not comprise a step of applying a hair treatment agent comprising a reducing agent or a strongly-alkaline hair treatment agent having pH 12 to 14 to the hair. Accordingly, it can be said that, in comparison to the aforementioned conventional hair deformation methods, the method of hair treatment of the present invention is also advantageous in that hair can be deformed without being damaged.

Preferred methods of hair treatments, which semi-permanently or permanently deform hair, include the following four patterns.

Pattern 1: Case where the Hair Treatment Agent is a One-Part Agent

1) Hair is optionally wetted with water.
2) The hair treatment agent of the present invention, which comprises the following components (A), (B) and (C), and further, optionally the following component (D), wherein the molar ratio of the content of the component (B) to the content of the component (A) is 0.01 to 5, is applied to hair to allow penetration thereof:
   Component (A): glyoxylic acid, or a hydrate or a salt thereof,
   Component (B): resorcin,
   Component (C): water, and
   Component (D): the resorcin derivative represented by the formula (1-1-3), and preferably, 4-alkyl resorcin.
3) The hair, to which the hair treatment agent has been applied, is optionally left for 1 minute or more and 1 hour or less. During this operation, the hair is optionally heated to a temperature of from 40° C. to 90° C.
4) The hair is heated and shaped at a temperature of from 50° C. to 250° C.,
5) The hair is optionally rinsed.
6) The hair is optionally heated at a temperature of from 40° C. to 230° C. and re-deformed.

Pattern 2: Case where the Hair Treatment Agent is a Two-Part Agent

1) Hair is optionally wetted with water.
2) The hair treatment agent of the present invention, in which a first agent comprising the following components (A) and (C) is mixed with a second agent comprising the following components (B) and (C), and further optionally the following component (D), so that the molar ratio of the content of the component (B) to the content of the component (A) can be from 0.01 to 5, is applied to hair to allow penetration thereof:
   Component (A): glyoxylic acid, or a hydrate or a salt thereof,
   Component (B): resorcin,
   Component (C): water, and
   Component (D): the resorcin derivative represented by the formula (1-1-3), and preferably, 4-alkyl resorcin.
3) The hair, to which the hair treatment agent has been applied, is optionally left for 1 minute or more and 1 hour or less. During this operation, the hair is optionally heated to a temperature of from 40° C. to 90° C.
4) The hair is heated and shaped at a temperature of from 50° C. to 250° C.
5) The hair is optionally rinsed.
6) The hair is optionally heated at a temperature of from 40° C. to 230° C. and re-deformed.

Pattern 3: Case where the Hair Treatment Agent is a Two-Part Agent

1) Hair is optionally wetted with water.
2) A first agent comprising the following components (A) and (C) is applied to hair to allow penetration thereof:
   Component (A): glyoxylic acid, or a hydrate or a salt thereof, and
   Component (C): water.
3) The hair is optionally left for 1 minute or more and 1 hour or less. During this operation, the hair is optionally heated to a temperature of from 40° C. to 90° C.
4) A second agent comprising the following components (B) and (C), and further optionally the following component (D), is applied onto the portion in hair, to which the first agent has been applied, so that the ratio of the molar number of the component (B) to the molar number of the component (A) can be from 0.01 to 5 to allow penetration thereof:
   Component (B): resorcin,
   Component (C): water, and
   Component (D): the resorcin derivative represented by the formula (1-1-3), and preferably, 4-alkyl resorcin.
5) The hair is optionally left for 1 minute or more and 1 hour or less, while it is optionally heated to a temperature of from 40° C. to 90° C.
6) The hair is heated and shaped at a temperature of from 50° C. to 250° C.
7) The hair is optionally rinsed.
8) The hair is optionally heated at a temperature of from 40° C. to 230° C. and re-deformed.

Pattern 4: Case where the Hair Treatment Agent is a Two-Part Agent

1) Hair is optionally wetted with water.
2) A second agent comprising the following components (B) and (C), and further optionally the following component (D), is applied to hair to allow penetration thereof:
   Component (B): resorcin,
   Component (C): water, and
   Component (D): the resorcin derivative represented by the formula (1-1-3), and preferably, 4-alkyl resorcin
3) The hair is optionally left for 1 minute or more and 1 hour or less. During this operation, the hair is optionally heated to a temperature of from 40° C. to 90° C.
4) A first agent comprising the following components (A) and (C) is applied onto the portion in hair, to which the second agent has been applied, so that the molar number ratio of the molar number of the component (B) to the molar number of the component (A) can be from 0.01 to 5 to allow penetration thereof:
   Component (A): glyoxylic acid, or a hydrate or a salt thereof, and
   Component (C): water.
5) The hair is optionally left for 1 minute or more and 1 hour or less, while it is optionally heated to a temperature of from 40° C. to 90° C.
6) The hair is heated and shaped at a temperature of from 50° C. to 250° C.
7) The hair is optionally rinsed.
8) The hair is optionally heated at a temperature of from 40° C. to 230° C., to re-deform the hair.

With regard to the aforementioned embodiments, preferred aspects of the present invention will be further disclosed below.

<1>
An agent for hair deforming treatment comprising the following components (A), (B) and (C):
(A) glyoxylic acid, or a hydrate or a salt thereof,
(B) resorcin, and
(C) water,
wherein the molar ratio of the content of the component (B) to the content of the component (A), (B)/(A), is 0.2 or more and 5 or less.

<2>
The agent for hair deforming treatment according to <1>, wherein the molar ratio of the content of the component (B) to the content of the component (A), (B)/(A), is preferably 0.3 or more, more preferably 0.4 or more, even more preferably 0.5 or more, and further preferably 0.7 or more, and also, it is preferably 2.5 or less, more preferably 2 or less, even more preferably 1.5 or less, and further preferably 1.2 or less.

<3>
The agent for hair deforming treatment according to <1> or <2>, wherein the content of the component (A) as an acid is preferably 1 mass % or more, more preferably 2 mass % or more, even more preferably 2.5 mass % or more, and further preferably 3 mass % or more, and also, it is preferably 30 mass % or less, more preferably 25 mass % or less, even more preferably 20 mass % or less, further preferably 15 mass % or less, and still further preferably 12 mass % or less.

<4>
The agent for hair deforming treatment according to any one of <1> to <3>, wherein the content of the component (B) is preferably 1 mass % or more, more preferably 2 mass % or more, even more preferably 3 mass % or more, further preferably 4 mass % or more, and still further preferably 5 mass % or more, and also, it is preferably 30 mass % or less, more preferably 25 mass % or less, even more preferably 20 mass % or less, and further preferably 17 mass % or less.

<5>
The agent for hair deforming treatment according to any one of <1> to <4>, which preferably further comprises a compound represented by the following formula (1) as a component (D):

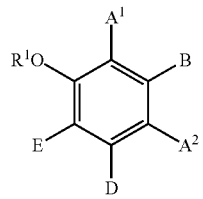

(1)

wherein
$R^1$ represents a hydrogen atom or a methyl group,
$A^1$ and $A^2$, which may be the same or different, each represent a hydrogen atom, a straight-chain or branched-chain alkyl group or alkenyl group containing from 1 to 12 carbon atoms, an optionally substituted aralkyl group or arylalkenyl group containing from 7 to 12 carbon atoms, a straight-chain or branched-chain alkoxy group or alkenyloxy group containing from 1 to 6 carbon atoms, a halogen atom, or —CO—$R^2$ (wherein $R^2$ represents a straight-chain or branched-chain alkyl group or alkenyl group containing from 1 to 12 carbon atoms, an optionally substituted aralkyl group or arylalkenyl group containing from 7 to 12 carbon atoms, or an optionally substituted aromatic hydrocarbon group containing from 6 to 12 carbon atoms),
B represents a hydrogen atom, a straight-chain or branched-chain alkyl group or alkenyl group containing from 1 to 12 carbon atoms, an optionally substituted aralkyl group or arylalkenyl group containing from 7 to 12 carbon atoms, —$OR^3$, or —$COOR^3$ (wherein $R^3$ represents a hydrogen atom, or a straight-chain or branched-chain alkyl group or alkenyl group containing from 1 to 6 carbon atoms),
D represents a hydrogen atom, a hydroxy group, a methyl group, or a straight-chain or branched-chain alkoxy group or alkenyloxy group containing from 1 to 12 carbon atoms, and
E represents a hydrogen atom, a hydroxy group, a straight-chain or branched-chain alkyl group or alkenyl group containing from 1 to 6 carbon atoms, or a straight-chain or branched-chain alkoxy group or alkenyloxy group containing from 1 to 6 carbon atoms,
provided that two or three of $A^1$, $A^2$, B and E are hydrogen atoms, and the remaining groups do not include sulfo groups, and that when D is a hydrogen atom or a methyl group, $A^1$ and B, or $A^2$ and B, together with two carbon atoms adjacent to them, form a benzene ring optionally substituted with a hydroxy group.

<6>
The agent for hair deforming treatment according to <5>, wherein the molar ratio of the content of the component (D) to the content of the component (B), (D)/(B), is preferably 0.1 or more, more preferably 0.15 or more, and even more preferably 0.2 or more, and also, it is preferably 3 or less, more preferably 2 or less, even more preferably 1 or less, and further preferably 0.4 or less.

<7>
The agent for hair deforming treatment according to <5> or <6>, wherein the molar ratio of the total content of the components (B) and (D) to the content of the component (A), [(B)+(D)]/(A), is preferably 0.2 or more, more preferably 0.3 or more, even more preferably 0.4 or more, further preferably 0.5 or more, and still further preferably 0.7 or more, and also, it is preferably 5 or less, more preferably 2.5 or less, even more preferably 2 or less, and further preferably 1.2 or less.

<8>
The agent for hair deforming treatment according to any one of <5> to <7>, wherein the total content of the component (B) and the component (D) is preferably 5 mass % or more, more preferably 10 mass % or more, and even more preferably 15 mass % or more, and also, it is preferably 30 mass % or less, more preferably 27 mass % or less, even more preferably 25 mass % or less, and further preferably 23 mass % or less.

<9>
The agent for hair deforming treatment according to any one of <5> to <8>, wherein the component (D) is preferably one or two or more selected from the group consisting of compounds represented by the following formulae (1-1), (1-2), and (1-3-a) or (1-3-b):

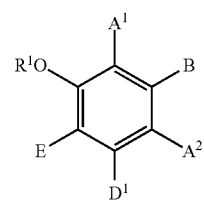

(1-1)

wherein $R^1$, $A^1$, $A^2$, B and E are as defined above, and $D^1$ represents a hydroxy group or a methoxy group,

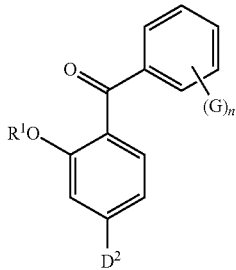

(1-2)

wherein $R^1$ is defined as that described above, $D^2$ represents a hydroxy group or an alkoxy group containing from 1 to 12 carbon atoms, G represents a hydroxy group, a straight-chain or branched-chain alkyl group or alkenyl group containing from 1 to 6 carbon atoms, or an alkoxy group containing from 1 to 6 carbon atoms, and n represents an integer of from 0 to 2, and

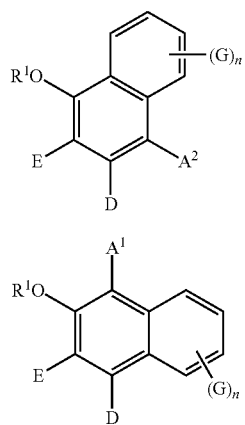

(1-3-a)

(1-3-b)

wherein $R^1$, $A^1$, E, D, G and n are as defined above.

<10>

The agent for hair deforming treatment according to <9>, wherein the compound represented by the formula (1-1) is preferably an m-dimethoxybenzene derivative represented by the following formula (1-1-1):

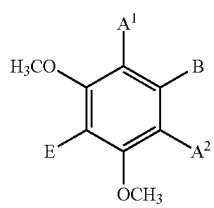

(1-1-1)

wherein $A^1$, $A^2$, B and E are as defined above.

<11>

The agent for hair deforming treatment according to <10>, wherein $A^1$ and $A^2$ each represent, preferably a hydrogen atom or a straight-chain or branched-chain alkyl group or alkenyl group containing from 1 to 4 carbon atoms, and more preferably a hydrogen atom.

<12>

The agent for hair deforming treatment according to <10> or <11>, wherein B represents: preferably a hydrogen atom, a straight-chain or branched-chain alkyl group or alkenyl group containing from 1 to 12 carbon atoms, an optionally substituted aralkyl group or arylalkenyl group containing from 7 to 12 carbon atoms, or —$OR^3$ (wherein $R^3$ represents a hydrogen atom, or a straight-chain or branched-chain alkyl group or alkenyl group containing from 1 to 6 carbon atoms); more preferably a hydrogen atom, an alkyl group or alkenyl group containing from 1 to 4 carbon atoms, an optionally substituted arylalkenyl group containing from 7 to 10 carbon atoms, or a hydroxy group; and even more preferably a hydrogen atom, an optionally substituted arylalkenyl group containing from 7 to 10 carbon atoms, or a hydroxy group.

<13>

The agent for hair deforming treatment according to any one of <10> to <12>, wherein E represents, preferably a hydrogen atom, or a straight-chain or branched-chain alkyl group or alkenyl group containing from 1 to 4 carbon atoms, and more preferably a hydrogen atom.

<14>

The agent for hair deforming treatment according to <9>, wherein the compound represented by the formula (1-1) is preferably an m-methoxyphenol derivative represented by the following formula (1-1-2):

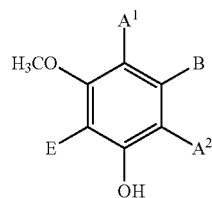

(1-1-2)

wherein $A^1$, $A^2$, B and E are as defined above.

<15>

The agent for hair deforming treatment according to <14>, wherein $A^1$ and $A^2$ each represent: preferably a hydrogen atom, a straight-chain or branched-chain alkyl group or alkenyl group containing from 1 to 12 carbon atoms, or an optionally substituted aralkyl group or arylalkenyl group containing from 7 to 12 carbon atoms; and more preferably a hydrogen atom, a straight-chain or branched-chain alkyl group containing from 1 to 6 carbon atoms, or an optionally substituted arylalkenyl group containing from 7 to 10 carbon atoms.

<16>

The agent for hair deforming treatment according to <14> or <15>, wherein B represents: preferably a hydrogen atom, a straight-chain or branched-chain alkyl group or alkenyl group containing from 1 to 12 carbon atoms, an optionally substituted aralkyl group or arylalkenyl group containing from 7 to 12 carbon atoms, or —$OR^3$ (wherein $R^3$ represents a hydrogen atom, or a straight-chain or branched-chain alkyl group or alkenyl group containing from 1 to 6 carbon atoms); more preferably a hydrogen atom, an alkyl group or alkenyl group containing from 1 to 4 carbon atoms, an optionally substituted arylalkenyl group containing from 7 to 10 carbon atoms, or a hydroxy group; and even more preferably a hydrogen atom, an optionally substituted arylalkenyl group containing from 7 to 10 carbon atoms, or a hydroxy group.

<17>

The agent for hair deforming treatment according to any one of <14> to <16>, wherein E represents: preferably a hydrogen atom, a hydroxy group, a straight-chain or branched-chain alkyl group or alkenyl group containing from 1 to 4 carbon atoms, or a straight-chain or branched-chain alkoxy group or alkenyloxy group containing from 1 to 4 carbon atoms; and more preferably a hydrogen atom or a hydroxy group.

<18>

The agent for hair deforming treatment according to <9>, wherein the compound represented by the formula (1-1) is preferably a resorcin derivative represented by the following formula (1-1-3):

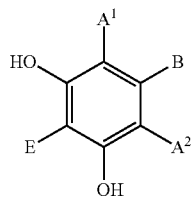

(1-1-3)

wherein $A^1$, $A^2$, B and E are as defined above.

<19>

The agent for hair deforming treatment according to <18>, wherein the resorcin derivative represented by the formula (1-1-3) is preferably a resorcin derivative represented by the following formula (i):

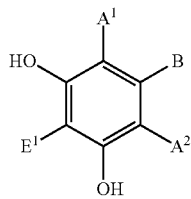

(i)

wherein $A^1$, $A^2$ and B are as defined above, and $E^1$ represents a hydroxy group, a straight-chain or branched-chain alkyl group or alkenyl group containing from 1 to 6 carbon atoms, or a straight-chain or branched-chain alkoxy group or alkenyloxy group containing from 1 to 6 carbon atoms.

<20>

The agent for hair deforming treatment according to <19>, wherein $A^1$ and $A^2$ each represent: preferably a hydrogen atom, or a straight-chain or branched-chain alkyl group or alkenyl group containing from 1 to 12 carbon atoms; and more preferably a hydrogen atom.

<21>

The agent for hair deforming treatment according to <19> or <20>, wherein B preferably represents a hydrogen atom, an optionally substituted aralkyl group or arylalkenyl group containing from 7 to 12 carbon atoms, or —$OR^3$ (wherein $R^3$ represents a hydrogen atom, or a straight-chain or branched-chain alkyl group or alkenyl group containing from 1 to 4 carbon atoms).

<22>

The agent for hair deforming treatment according to any one of <18> to <21>, wherein $E^1$ preferably represents a hydroxy group, a straight-chain or branched-chain alkyl group or alkenyl group containing from 1 to 4 carbon atoms, or a straight-chain or branched-chain alkoxy group or alkenyloxy group containing from 1 to 4 carbon atoms.

<23>

The agent for hair deforming treatment according to any one of <19> to <22>, wherein the resorcin derivative represented by the formula (i) is preferably 2-alkyl resorcin, pyrogallol, 2-methoxy resorcin, gallic acid or gallic acid ester, and more preferably 2-alkyl resorcin, gallic acid or gallic acid ester.

<24>

The agent for hair deforming treatment according to <18>, wherein the resorcin derivative represented by the formula (1-1-3) is preferably a resorcin derivative represented by the following (ii-1):

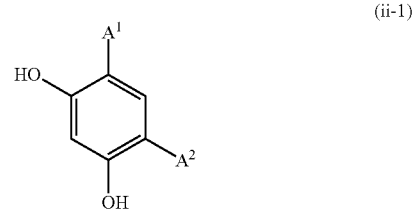

(ii-1)

wherein $A^1$ and $A^2$ are as defined above.

<25>

The agent for hair deforming treatment according to <24>, wherein the resorcin derivative represented by the formula (ii-1) represents: preferably 4-alkyl resorcin, 4-alkenyl resorcin, 4-aralkyl resorcin, 4-hydroxyaralkyl resorcin, 4-arylalkenyl resorcin, 4-hydroxyarylalkenyl resorcin, 4-(1-methylnaphthyl) resorcin, 4-alkoxy resorcin, halogenated resorcin, 4-alkanoyl resorcin, or 4-arylalkanoyl resorcin; more preferably 4-alkyl resorcin, 4-aralkyl resorcin, halogenated resorcin, 4-alkanoyl resorcin, or 4-arylalkanoyl resorcin; and even more preferably 4-alkyl resorcin or 4-aralkyl resorcin.

<26>

The agent for hair deforming treatment according to <18>, wherein the resorcin derivative represented by the formula (1-1-3) is preferably a resorcin derivative represented by the following formula (ii-2):

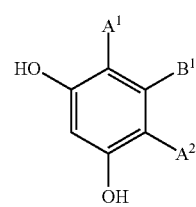

(ii-2)

wherein $A^1$ and $A^2$ are as defined above, and $B^1$ represents a straight-chain or branched-chain alkyl group or alkenyl group containing from 1 to 12 carbon atoms, an optionally substituted aralkyl group or arylalkenyl group containing from 7 to 12 carbon atoms, —$OR^3$, or —$COOR^3$ (wherein $R^3$ represents a hydrogen atom, or a straight-chain or branched-chain alkyl group or alkenyl group containing from 1 to 6 carbon atoms.

<27>
The agent for hair deforming treatment according to <26>, wherein the resorcin derivative represented by the formula (ii-2) is preferably a resorcin derivative represented by the following formula (ii-2-a):

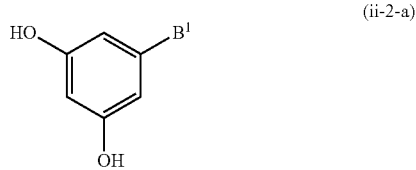

(ii-2-a)

wherein $B^1$ is defined as that described above.
<28>
The agent for hair deforming treatment according to <27>, wherein the resorcin derivative represented by the formula (ii-2-a) represents: preferably 5-alkyl resorcin, 5-alkenyl resorcin, phloroglucinol, 5-alkoxybenzene-1,3-diol, 3,5-dihydroxybenzoic acid, 3,5-dihydroxybenzoic acid ester, 5-aralkyl resorcin, 5-hydroxyaralkyl resorcin, 5-arylalkenyl resorcin, or 5-hydroxyarylalkenyl resorcin; and more preferably 5-alkyl resorcin, 5-aralkyl resorcin, 5-hydroxyaralkyl resorcin, or 5-hydroxyarylalkenyl resorcin.
<29>
The agent for hair deforming treatment according to <26>, wherein the resorcin derivative represented by the formula (ii-2) is preferably a resorcin derivative represented by the following formula (ii-2-b):

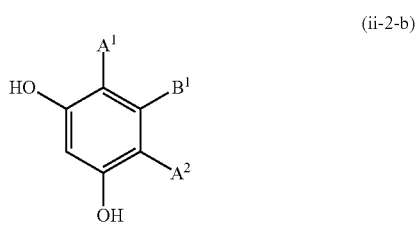

(ii-2-b)

wherein $A^1$, $A^2$ and $B^1$ are as defined above.
<30>
The agent for hair deforming treatment according to <29>, wherein $A^1$ and $A^2$ each represent: preferably a hydrogen atom, a straight-chain or branched-chain alkyl group or alkenyl group containing from 1 to 4 carbon atoms, or an alkoxy group or alkenyloxy group containing from 1 to 4 carbon atoms.
<31>
The agent for hair deforming treatment according to <30>, wherein the resorcin derivative represented by the formula (ii-2-b) represents: preferably 2-alkylbenzene-1,3,5-triol, phloroglucin acid ester, or 3,5-dihydroxybenzoic acid ester; and more preferably phloroglucin acid ester.
<32>
The agent for hair deforming treatment according to <9>, wherein the benzophenone derivative represented by the formula (1-2) represents: preferably benzophenone-1, benzophenone-2, benzophenone-3, benzophenone-6, benzophenone-8, benzophenone-10, or benzophenone-12; and more preferably benzophenone-12.
<33>
The agent for hair deforming treatment according to <9>, wherein the naphthol derivative represented by the formula (1-3-a) or (1-3-b) is a naphthol derivative, wherein, in the formula (1-3-a) or (1-3-b), $R^1$ represents preferably a hydrogen atom, or an alkyl group or alkenyl containing from 1 to 4 carbon atoms, and more preferably a hydrogen atom.
<34>
The agent for hair deforming treatment according to <33>, wherein the naphthol derivative represented by the formula (1-3-a) or (1-3-b) is a naphthol derivative, wherein, in the formula (1-3-a) or (1-3-b), $A^1$ and $A^2$ each represent, preferably a hydrogen atom, a hydroxy group, a straight-chain or branched-chain alkyl group containing from 1 to 4 carbon atoms, or an alkoxy group containing from 1 to 4 carbon atoms, and more preferably a hydrogen atom or a hydroxy group.
<35>
The agent for hair deforming treatment according to <33> or <34>, wherein the naphthol derivative represented by the formula (1-3-a) or (1-3-b) is a naphthol derivative, wherein, in the formula (1-3-a) or (1-3-b), D preferably represents a hydrogen atom, a hydroxy group, a straight-chain or branched-chain alkyl group containing from 1 to 4 carbon atoms, or an alkoxy group containing from 1 to 4 carbon atoms.
<36>
The agent for hair deforming treatment according to any one of <33> to <35>, wherein the naphthol derivative represented by the formula (1-3-a) or (1-3-b) is a naphthol derivative, wherein, in the formula (1-3-a) or (1-3-b), E preferably represents a hydrogen atom, a hydroxy group, or an alkyl group containing from 1 to 4 carbon atoms or an alkoxy group containing from 1 to 4 carbon atoms.
<37>
The agent for hair deforming treatment according to any one of <33> to <36>, wherein the naphthol derivative represented by the formula (1-3-a) or (1-3-b) is 1-naphthol, 2-naphthol, 3-methylnaphthalene-1-ol, naphthalene-1,4-diol, naphthalene-1,5-diol, or naphthalene-1,8-diol.
<38>
The agent for hair deforming treatment according to any one of <5> to <37>, wherein the component (D) is: preferably one or two or more selected from the group consisting of the m-dimethoxybenzene derivative represented by the formula (1-1-1), the resorcin derivative represented by the formula (1-1-3), the benzophenone derivative represented by the formula (1-2), and the naphthol derivative represented by the formula (1-3-a) or (1-3-b); more preferably one or two or more selected from the group consisting of 2-methyl resorcin, 4-chloro resorcin, 4-alkyl resorcin, 4-aralkyl resorcin, 4-acylated resorcin, 5-alkyl resorcin, 5-aralkyl resorcin, 5-hydroxyarylalkenyl resorcin, phloroglucin acid ester, gallic acid, and gallic acid ester; even more preferably one or two or more selected from the group consisting of 4-butyl resorcin (trivial name: Rucinol), 4-(1-phenylethyl) resorcin (trivial name: Symwhite 377), 5-(hydroxyphenylethenyl) resorcin (trivial name: resveratrol), 3-hydroxyphenyl-1-(benzene-2,4,6-triol)propan-1-one (trivial name: Phloretin), 4-(2,4-dihydroxybenzoyl) resorcin (trivial name: Benzophenone-2), 5-(hydroxyphenylethenyl)-1,3-dimethoxybenzene (trivial name: Pterostilbene), and 1-naphthol; and further preferably one or two or more selected from the group consisting of 4-butyl resorcin, 4-(1-phenylethyl) resorcin, and 4-n-hexyl resorcin.
<39>
The agent for hair deforming treatment according to any one of <1> to <38>, wherein the pH thereof is preferably 4 or less, more preferably 3 or less, even more preferably 2.5 or less, and further preferably 2 or less, and also, it is preferably 1 or more, more preferably 1.2 or more, and more preferably 1.5 or more.

<40>
The agent for hair deforming treatment according to any one of <1> to <39>, wherein the molecular weight of the component (D) is preferably 120 or more, and from the viewpoint of permeability into hair, it is preferably 1000 or less, more preferably 500 or less, and even more preferably 300 or less.

<41>
The agent for hair deforming treatment according to any one of <1> to <40>, which comprises an aromatic compound having at least one amino group, having another amino group or a hydroxy group at the ortho position or para position of the one amino group, and also having a closed-shell quinoid structure when oxidized, in an amount of preferably less than 0.1 mass %, and more preferably less than 0.01 mass %, and even more preferably, the agent for hair deforming treatment does not comprise the compound therein.

<42>
The agent for hair deforming treatment according to any one of <1> to <41>, wherein, preferably, deformation of hair is not caused by the cleavage and recombination of the S—S bond of hair proteins.

<43>
The agent for hair deforming treatment according to any one of <1> to <42>, wherein the total amount of components for reducing proteins in hair is preferably less than 0.1 mass %, and more preferably less than 0.01 mass, and even more preferably, the agent for hair deforming treatment does not comprise the compounds therein.

<44>
The agent for hair deforming treatment according to <43>, wherein the components for reducing proteins in hair are thiol, hydrogen sulfite, and salts thereof.

<45>
The agent for hair deforming treatment according to <44>, wherein the thiol is preferably thioglycolic acid, dithioglycolic acid, cysteine, acetylcysteine, or butyrolactonethiol.

<46>
The agent for hair deforming treatment according to any one of <1> to <45>, which is preferably a multi-part agent comprising a first agent comprising the component (A) and a second agent comprising the component (B).

<47>
The agent for hair deforming treatment according to <46>, wherein the content of the component (A) in the first agent is preferably 1 mass % or more, more preferably 2 mass % or more, even more preferably 2.5 mass % or more, and further preferably 3 mass % or more, and also, it is preferably 30 mass % or less, more preferably 25 mass % or less, even more preferably 20 mass % or less, further preferably 15 mass % or less, and still further preferably 12 mass % or less.

<48>
The agent for hair deforming treatment according to <46> or <47>, wherein the content of the component (B) in the second agent is preferably 1 mass % or more, more preferably 2 mass % or more, even more preferably 3 mass % or more, further preferably 4 mass % or more, and still further preferably 5 mass % or more, and also, it is preferably 30 mass % or less, more preferably 25 mass % or less, even more preferably 20 mass % or less, and further preferably 17 mass % or less.

<49>
The agent for hair deforming treatment according to any one of <46> to <48>, which is preferably a multi-part agent comprising a first agent comprising the component (A) and a second agent comprising the component (B) and the component (D).

<50>
The agent for hair deforming treatment according to <49>, wherein the mass ratio of the content of the component (D) to the content of the component (B) in the second agent, (D)/(B), is preferably 0.1 or more, more preferably 0.15 or more, and even more preferably 0.2 or more, and also, it is preferably 3 or less, more preferably 2 or less, even more preferably 1 or less, and further preferably 0.4 or less.

<51>
The agent for hair deforming treatment according to <46> or <50>, wherein the pH of the first agent is preferably 4 or less, more preferably 3 or less, even more preferably 2.5 or less, and further preferably 2 or less, and also, it is preferably 1 or more, more preferably 1.2 or more, and even more preferably 1.5 or more.

<52>
The multi-part agent for hair deforming treatment according to any one of <46> to <51>, wherein the composition after completion of the mixing of the parts is the composition according to any one of <1> to <45>.

<53>
A method of hair treatment for semi-permanently or permanently deforming the shape of hair, which comprises the following steps (i) and (ii):
(i) applying the agent for hair deforming treatment according to any one of <1> to <52> to hair, and then allowing the agent to penetrate into the hair, and
(ii) heating and shaping the hair into which the agent for hair deforming treatment has penetrated.

<54>
The method of hair deforming treatment according to <53>, wherein the step (i) is preferably a step of mixing the first agent of the multi-part agent for hair deforming treatment according to any one of <46> to <52> with the second agent thereof, and then applying the obtained mixture to hair.

<55>
The method of hair deforming treatment according to <53>, wherein the step (i) is preferably a step of applying one of the first agent and the second agent in the multi-part agent for hair deforming treatment according to any one of <46> to <52> to hair, and then applying the other part onto the portion applied.

<56>
The method of hair deforming treatment according to <55>, wherein the step (i) is preferably a step of applying the second agent comprising the component (B), and then applying the first agent comprising the component (A) onto the portion applied.

<57>
The method of hair treatment according to <55> or <56>, wherein the molar ratio of the amount of the component (B) comprised in the second agent applied to hair to the amount of the component (A) comprised in the first agent applied to hair, (B)/(A), is preferably 0.2 or more, more preferably 0.3 or more, even more preferably 0.4 or more, further preferably 0.5 or more, and still further preferably 0.7 or more, and also, it is preferably 5 or less, more preferably 2.5 or less, even more preferably 2 or less, further preferably 1.5 or less, and still further preferably 1.2 or less.

<58>

The method of hair treatment according to any one of <55> to <57>, wherein the molar ratio of the total content of the components (B) and (D) in the second agent applied to hair to the amount of the component (A) in the first agent applied to hair, [(B)+(D)]/(A), is preferably 0.2 or more, more preferably 0.3 or more, even more preferably 0.4 or more, further preferably 0.5 or more, and still further preferably 0.7 or more, and also, it is preferably 5 or less, more preferably 2.5 or less, even more preferably 2 or less, further preferably 1.5 or less, and still further preferably 1.2 or less.

<59>

The method of hair deforming treatment according to any one of <55> to <58>, which preferably comprises a step of leaving hair, to which one of the first agent and the second agent has been applied, between the step of applying the one part to the hair and the step of applying the other part onto the portion applied.

<60>

The method of hair treatment according to <59>, wherein when the hair to which one part has been applied is left, the hair is left, preferably while being heated at a temperature of from 40° C. to 90° C.

<61>

The method of hair treatment according to any one of <53> to <60>, which preferably comprises a step of wetting hair before the step (i).

<62>

The method of hair treatment according to any one of <53> to <61>, wherein the heating temperature in the step (ii) is preferably 50° C. or higher, more preferably 60° C. or higher, and even more preferably 80° C. or higher, and also, it is preferably 250° C. or lower, more preferably 240° C. or lower, and even more preferably 230° C. or lower.

<63>

The method of hair treatment according to any one of <53> to <62>, wherein the step (ii) is preferably carried out under an environment in which evaporation of water is suppressed.

<64>

The method of hair treatment according to any one of <53> to <63>, which preferably does not comprise a step of applying a hair treatment agent comprising a reducing agent or a strongly-alkaline hair treatment agent having pH 12 to 14 to the hair.

<65>

The method of hair treatment according to any one of <53> to <64>, wherein the mass of the agent for hair deforming treatment applied to hair in the step (i) is, at a bath ratio of the mass of the agent for hair deforming treatment to the mass of the hair (the mass of the agent for hair deforming treatment/the mass of the hair), preferably 0.05 or more, more preferably 0.1 or more, even more preferably 0.25 or more, and further preferably 0.5 or more, and also, it is preferably 5 or less, more preferably 3 or less, and even more preferably 2 or less.

<66>

The method of hair treatment according to any one of <53> to <65>, wherein the heating time in the step (ii) is preferably 1 second or more, more preferably 5 seconds or more, even more preferably 1 minute or more, further preferably 5 minutes or more, still further preferably 15 minutes or more, and still further preferably 30 minutes or more, and also, it is preferably 2 hours or less, more preferably 1 hour or less, and even more preferably 45 minutes or less.

<67>

The method of hair treatment according to any one of <53> to <66>, which preferably comprises a step of leaving hair, to which the hair treatment agent has been applied, between the step (i) and the step (ii).

<68>

The method of hair treatment according to <67>, wherein the leaving time is preferably 1 minute or more, more preferably 3 minutes or more, and even more preferably 5 minutes or more, and also, it is preferably 1 hour or less, more preferably 30 minutes or less, and even more preferably 20 minutes or less.

<69>

The method of hair treatment according to <67> or <68>, wherein hair is preferably heated at a temperature of from 40° C. to 90° C. during the leaving time between the step (i) and the step (ii).

<70>

The method of hair treatment according to any one of <53> to <69>, which preferably does not comprise a step of rinsing hair, to which the hair treatment agent has been applied, between the step (i) and the step (ii).

<71>

The method of hair treatment according to any one of <53> to <70>, which preferably comprises a step of rinsing hair after the step (ii).

<72>

The method of hair treatment according to any one of <53> to <71>, wherein hair is preferably re-deformed into a different shape by heating, after the step (ii).

<73>

The method of hair treatment according to <72>, wherein preferably the agent for hair deforming treatment is not applied, when hair is re-deformed.

<74>

The method of hair treatment according to <72> or <73>, wherein the heating temperature when hair is re-deformed is preferably 30° C. or higher, and more preferably 40° C. or higher, and also it is preferably 230° C. or lower, more preferably 220° C. or lower, and even more preferably 210° C. or lower.

<75>

Use of the composition according to any one of <1> to <52> for semi-permanent or permanent hair deformation.

EXAMPLES

Examples 1 to 12 and Comparative Examples 1 to 6

The treatment agents shown in Table 1 were prepared, and the following three-step hair treatment processes were then carried out using the agents. The shape-giving effect of each agent at each step was evaluated. The results are also shown in Table 1. It is to be noted that the pH of each composition was measured by leaving the prepared composition at a room temperature (25° C.) and then measuring the pH with a pH meter (manufactured by HORIBA/Model No.: F-52).

<I: Imparting a Semi-Permanent Curly Shape>

1. A 25 cm-long tress, which consisted of 0.5 g of Caucasian straight hair (untreated hair), was wetted with tap water at 30° C. for 30 seconds, and the wet tress was then wound around a plastic rod with a diameter of 14 mm, and fixed with a clip.

2. 1 g of the treatment agent was applied to the tress wound around the rod, and the entire rod was then covered with a plastic film for hermetical sealing. The tress was then heated for 1 hour in an oven, which was set at 90° C.

3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof being held, and water was then drained off by light shaking.
6. The tress was hung and allowed to stand in a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.
(Evaluation Criteria)
A: The curl diameter is 1 time or more and less than 2 times as large as the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has been maintained, and the hair shape has not changed from before the treatment.
<II: Imparting a Semi-Permanent Straight Shape to Semi-Permanent Curly-Shaped Hair>
1. The tress, which had been evaluated in <I: Imparting a semi-permanent curly shape> above, was combed to detangle it, and an iron with an actual temperature of 180° C. was slid through the tress at a rate of 5 cm/sec six times.
2. The tress was rinsed with running tap water at 30° C. for 30 seconds, and a shampoo for evaluation was lathered on the tress for 60 seconds. Thereafter, the tress was rinsed with running tap water at 30° C. for 30 seconds, and it was then dried with a towel.
3. The tress was dried, while being shaken, so that the natural shape of hair could appear (wherein dryer was not used), and it was then combed. Thereafter, the tress was hung, and was then visually observed from the side.
(Evaluation Criteria)
A: The curl has not remained, and the hair is completely deformed into straight hair.
B: The curl has become weaker than before the treatment with a flat iron, but the hair has not been completely deformed into straight hair.
C: The curly hair has been maintained, and the hair shape has not changed from before the treatment.

<III: Imparting a Semi-Permanent Curly Shape to Semi-Permanent Straight-Shaped Hair>
1. The tress, which had been evaluated in <II: Imparting a semi-permanent straight shape to semi-permanent curly-shaped hair> above, was wetted with tap water at 30° C. for 30 seconds, and the wet tress was then wound around a plastic rod with a diameter of 14 mm, and fixed with a clip.
2. The rod was entirely covered with a plastic film for hermetical sealing. Thereafter, the tress was heated for 1 hour in an oven, which was set at 40° C.
3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking.
6. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.
(Evaluation Criteria)
A: The curl diameter is 1 time or more and less than 2 times as large as the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has been maintained, and the hair shape has not changed from before the treatment.
<Formulation of Shampoo for Evaluation>

| Component | (mass %) |
| --- | --- |
| Sodium laureth sulfate | 15.5 |
| Lauramide DEA | 1.5 |
| Sodium benzoate | 0.5 |
| EDTA-2Na | 0.3 |
| Phosphoric acid | Amount to be adjusted to pH7 |
| Deionized water | balance |
| Total | 100 |

TABLE 1

| | | | Example | | | | | | | | |
| --- | --- | --- | --- | --- | --- | --- | --- | --- | --- | --- | --- |
| | | | 1 | 2 | 3 | 4 | 5 | 6 | 7 | 8 | 9 |
| Formulation [mass %] | (A) | Glyoxylic acid | 10 | 10 | 10 | 10 | 10 | 20 | 5 | 10 | 10 |
| | (A') | Glyceraldehyde | — | — | — | — | — | — | — | — | — |
| | (B) | Resorcin | 5 | 10 | 15 | 20 | 30 | 30 | 7.5 | 13 | 7.5 |
| | (B') | Catechol | — | — | — | — | — | — | — | — | — |
| | | Hydroquinone | — | — | — | — | — | — | — | — | — |
| | | Sodium 2.2'-dihydroxy-4.4'-dimethoxybenzophenone-5,5'-disulfonate | — | — | — | — | — | — | — | — | — |
| | (D) | 4-n-Butyl resorcin (Rucinol) | — | — | — | — | — | — | — | — | 11.25 |
| | | 4-n-Hexyl resorcin | — | — | — | — | — | — | — | 3.53 | — |
| | | 4-Phenylethyl resorcin (Symwhite) | — | — | — | — | — | — | — | — | — |

TABLE 1-continued

|  |  |  |  |  |  |  |  |  |  |  |
|---|---|---|---|---|---|---|---|---|---|---|
| Others | Hydrochloric acid | — | — | — | — | — | — | — | — | — |
|  | Sodium hydroxide |  |  |  |  | (*1) |  |  |  |  |
| (C) | Deionized water |  |  |  |  | Balance |  |  |  |  |
|  | Total |  |  |  |  | 100 |  |  |  |  |
|  | pH |  |  |  |  | 2.0 |  |  |  |  |
| Component molar ratio | (B)/(A) or (B')/(A) or (B)/(A') | 0.34 | 0.67 | 1.0 | 1.3 | 2.0 | 1.0 | 1.0 | 0.87 | 0.50 |
|  | [(B) + (D)]/(A) | 0.34 | 0.67 | 1.0 | 1.3 | 2.0 | 1.0 | 1.0 | 1.0 | 1.0 |
|  | (D)/(B) | 0.0 | 0.0 | 0.0 | 0.0 | 0.0 | 0.0 | 0.0 | 0.15 | 1.0 |
| Evaluation results | I. Imparting a semi-permanent curly shape | D | C | B | C | D | A | D | B | A |
|  | II. Imparting a semi-permanent straight shape to semi-permanent curly-shaped hair | A | A | A | A | A | A | A | A | A |
|  | III. Imparting a semi-permanent curly shape to semi-permanent straight-shaped hair | C | C | B | C | D | B | D | B | B |

|  |  |  | Example | | | Comparative Example | | | | | |
|---|---|---|---|---|---|---|---|---|---|---|---|
|  |  |  | 10 | 11 | 12 | 1 | 2 | 3 | 4 | 5 | 6 |
| Formulation [mass %] | (A) | Glyoxylic acid | 10 | 10 | 10 | 10 | 10 | 10 | — | 20 | — |
|  | (A') | Glyceraldehyde | — | — | — | — | — | — | 20 | — | — |
|  | (B) | Resorcin | 11.25 | 11.25 | 7.5 | — | — | — | 24.4 | — | 20 |
|  | (B') | Catechol | — | — | — | 15 | — | — | — | — | — |
|  |  | Hydroquinone | — | — | — | — | 5 | — | — | — | — |
|  |  | Sodium 2.2'-dihydroxy-4.4'-dimethoxybenzophenone-5,5'-disulfonate | — | — | — | — | — | 6.5 | — | — | — |
|  | (D) | 4-n-Butyl resorcin (Rucinol) | 5.6 | — | 6.8 | — | — | — | — | — | — |
|  |  | 4-n-Hexyl resorcin | — | — | — | — | — | — | — | — | — |
|  |  | 4-Phenylethyl resorcin (Symwhite) | — | 7.2 | 5.9 | — | — | — | — | — | — |
|  | Others | Hydrochloric acid | — | — | — | — | — | — | (*1) | — | — |
|  |  | Sodium hydroxide |  |  |  |  |  |  | — | (*1) |  |
|  | (C) | Deionized water |  |  |  |  | Balance |  |  |  |  |
|  |  | Total |  |  |  |  | 100 |  |  |  |  |
|  |  | pH |  |  |  |  | 2.0 |  |  |  |  |
| Component molar ratio |  | (B)/(A) or (B')/(A) or (B)/(A') | 0.76 | 0.76 | 0.50 | 1.0 | 0.34 | 0.10 | 1.0 | 0.0 | — |
|  |  | [(B) + (D)]/(A) | 1.0 | 1.0 | 1.0 | 0.0 | 0.0 | 0.0 | — | 0.0 | — |
|  |  | (D)/(B) | 0.33 | 0.33 | 1.0 | — | — | — | 0.0 | — | 0.0 |
| Evaluation results |  | I. Imparting a semi-permanent curly shape | A | A | A | E | E | E | E | E | E |
|  |  | II. Imparting a semi-permanent straight shape to semi-permanent curly-shaped hair | A | A | A | *2 | *2 | *2 | *2 | *2 | *2 |
|  |  | III. Imparting a semi-permanent curly shape to semi-permanent straight-shaped hair | A | A | A | *2 | *2 | *2 | *2 | *2 | *2 |

(*1): Amount for adjusting to pH 2.0
*2: Since curly shape could not be provided to hair in Evaluation I, not evaluated.

Examples 13 and 14

The treatment agents shown in Table 2 were prepared, and the following three-step hair treatment processes were then carried out using the agents. The shape-giving effect of each agent at each step was evaluated. The results are also shown in Table 2.

<I: Imparting a Semi-Permanent Curly Shape>
1. A 25 cm-long tress, which consisted of 0.5 g of Caucasian straight hair (untreated hair), was wetted with tap water at 30° C. for 30 seconds, and the wet tress was then wound around a plastic rod with a diameter of 14 mm, and fixed with a clip.
2. The tress wound around the rod was immersed in 40 g of the treatment agent, and as it was, it was heated for 3 hours in an oven, which was set at 90° C.
3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof being held, and water was then drained off by light shaking.
6. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.

(Evaluation Criteria)
A: The curl diameter is 1 time or more and less than 2 times as large as the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has been maintained, and the hair shape has not changed from before the treatment.

<II: Imparting a Semi-Permanent Straight Shape to Semi-Permanent Curly-Shaped Hair>
1. The tress, which had been evaluated in terms of the effect of giving an initial hair shape, was combed to detangle it, and thereafter, a flat iron with an actual temperature of 180° C. was slid through the tress at a rate of 5 cm/sec six times.

2. Tress was rinsed with running tap water at 30° C. for 30 seconds, and a shampoo for evaluation was then lathered on the tress for 60 seconds. Thereafter, the tress was rinsed with running tap water at 30° C. for 30 seconds, and was then dried with a towel.

3. The tress was dried, while being shaken, so that the natural shape of hair could appear (wherein dryer was not used), and it was then combed. The tress was hung, and was then visually observed from the side.

(Evaluation Criteria)

A: The curl diameter is 1 time or more and less than 2 times as large as the used rod (diameter: 14 mm)

B: The curl diameter is 2 times or more and less than 3 times as large as the used rod (diameter: 14 mm)

C: The curl diameter is 3 times or more and less than 4 times as large as the used rod (diameter: 14 mm)

D: The curl diameter is 4 times or more and less than 50 times as large as the used rod (diameter: 14 mm)

E: Straight hair has been maintained, and the hair shape has not changed from before the treatment.

TABLE 2

|  |  |  | Example | |
|---|---|---|---|---|
|  |  |  | 13 | 14 |
| Formulation [mass %] | (A) | Glyoxylic acid | 2.5 | 3.3 |
|  | (B) | Resorcin | 3.75 | 5 |
|  | Others | Sodium hydroxide |  (*1) | |
|  | (C) | Deionized water | Balance | |
|  |  | Total | 100 | |
|  |  | pH | 2.0 | |
| Component molar ratio (B)/(A) |  |  | 1.00 | |
| Evaluation results | I. Imparting a semi-permanent curly shape | | C | A |
|  | II. Imparting a semi-permanent straight shape to semi-permanent curly-shaped hair | | A | A |
|  | III. Imparting a semi-permanent curly shape to semi-permanent straight-shaped hair | | C | A |

*(1): Amount for adjusting to pH 2.0

(Evaluation Criteria)
A: The curl has not remained, and the hair is completely deformed into straight hair.
B: The curl has become weaker than before the treatment with a flat iron, but the hair has not been completely deformed into straight hair.
C: The curly hair has been maintained, and the hair shape has not changed from before the treatment.

<III: Imparting a Semi-Permanent Curly Shape to Semi-Permanent Straight-Shaped Hair>

1. The tress, which had been evaluated in <II: Imparting a semi-permanent straight shape to semi-permanent curly-shaped hair> above, was wetted with tap water at 30° C. for 30 seconds, and the wet tress was then wound around a plastic rod with a diameter of 14 mm, and fixed with a clip.

2. The rod was entirely covered with a plastic film for hermetical sealing. Thereafter, the tress was heated for 1 hour in an oven, which was set at 40° C.

3. The tress was removed from the oven, and cooled to a room temperature.

4. The tress was removed from the rod, and was then rinsed with running tap water at 30° C. for 30 seconds. Thereafter, a shampoo for evaluation was lathered on the tress for 60 seconds.

5. The tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking.

6. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.

Example 15

The treatment agent shown in Table 3 was prepared, and the following three-step hair treatment processes were then carried out using the agent. The shape-giving effect of each agent at each treatment was evaluated. The results are also shown in Table 3.

<I: Imparting a Semi-Permanent Straight Shape>

1. A tress consisting of slightly spread, straight hair from Caucasian race (untreated hair) (weight: 0.5 g/length: 25 cm) was wetted with tap water at 30° C. for 30 seconds, and the wet tress was then wound around a plastic rod with a diameter of 14 mm, and fixed with a clip.

2. 1.0 g of the treatment agent was applied to the tress wound around the rod, and the entire rod was covered with a plastic film for hermetical sealing, and heated for 1 hour in an oven, which was set at 40° C.

3. The tress was removed from the oven, and cooled to a room temperature.

4. The plastic film was uncovered, and the tress was then removed from the rod. Water was lightly removed with a towel, and the tress was then dried with hot air from a dryer, until it was completely dried.

5. The tress was combed to detangle it, and a flat iron with an actual temperature of 230° C. was slid through the tress at a rate of 5 cm/sec six times, so that the style of straight hair was completely formed from the roots to the tips of the tress.

6. The tress was rinsed with running tap water at 30° C. for 30 seconds. Thereafter, a shampoo for evaluation was lathered on the tress for 60 seconds. After that, the tress was rinsed with running tap water at 30° C. for 30 seconds, and was then dried with a towel.

7. The tress was dried, while being shaken, so that the shape of hair could directly appear, and it was then combed. Thereafter, the tress was hung, and was then visually observed from the side.
(Evaluation Criteria)
A: The spreading of the tress disappears, and completely straight hair is maintained from the roots to the tips of the tress.
B: Although the tress is straight hair, in which the spreading of the tress is suppressed, it is slightly spread.
C: The spreading of the tress is equivalent to that of untreated hair.

<II: Imparting a Semi-Permanent Curly Shape to Semi-Permanent Straight-Shaped Hair>
1. The tress, which had been evaluated in <I: Imparting a semi-permanent straight shape> above, was wetted with tap water at 30° C. for 30 seconds, and the wet tress was then wound around a plastic rod with a diameter of 14 mm, and fixed with a clip.
2. The rod was entirely covered with a plastic film for hermetical sealing. Thereafter, the tress was heated for 1 hour in an oven, which was set at 40° C.
3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof being held, and water was then drained off by light shaking.
6. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.
(Evaluation Criteria)
A: The curl diameter is 1 time or more and less than 2 times the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has remained, and the hair shape has not changed from before the treatment.

<III: Imparting a Semi-Permanent Straight Shape to Semi-Permanent Curly-Shaped Hair>
1. The tress, which had been evaluated in <II: Imparting a semi-permanent curly shape to semi-permanent straight-shaped hair> above, was detangled by combing, and a flat iron with an actual temperature of 180° C. was then slid through the tress at a rate of 5 cm/sec six times.
2. The tress was rinsed with running tap water at 30° C. for 30 seconds, and a shampoo for evaluation was then lathered on the tress for 60 seconds. Thereafter, the tress was rinsed with running tap water at 30° C. for 30 seconds, and was then dried with a towel.
3. The tress was dried, while being shaken, so that the natural shape of hair could appear (wherein dryer was not used), and it was then combed. Thereafter, the tress was hung, and was then visually observed from the side.
(Evaluation Criteria)
A: The curl has not remained, and the hair has been completely deformed into straight hair
B: The curl has become weaker than before the treatment with a flat iron, but the hair has not been completely deformed into straight hair.
C: The curly hair has been maintained, and the hair shape has not changed from before the treatment.

TABLE 3

|  |  |  | Example 15 |
|---|---|---|---|
| Formulation [mass %] | (A) | Glyoxylic acid | 10 |
|  | (B) | Resorcin | 15 |
|  | Others | Sodium hydroxide | (*1) |
|  | (C) | Deionized water | Balance |
|  |  | Total | 100 |
|  |  | pH | 2.0 |
| Component molar ratio (B)/(A) |  |  | 1.0 |
| Evaluation results | I. Imparting a semi-permanent straight shape |  | A |
|  | II. Imparting a semi-permanent curly shape to semi-permanent straight-shaped hair |  | B |
|  | III. Imparting a semi-permanent straight shape to semi-permanent curly-shaped hair |  | A |

*(1): Amount for adjusting to pH 2.0

Example 16

The two-part treatment agent shown in Table 4 was prepared, and the following three-step hair treatment processes were then carried out using the agent. The effect of the agent to provide each hair shape was evaluated. The results are also shown in Table 4.

<I: Imparting a Semi-Permanent Curly Shape>

1. A 25 cm-long tress, which consisted of 0.5 g of Caucasian straight hair (untreated hair), was wetted with tap water at 30° C. for 30 seconds, and the wet tress was then wound around a plastic rod with a diameter of 14 mm, and fixed with a clip.
2. 1 g of the formulated first agent was applied to the tress wound around the rod. The rod was entirely covered with a plastic film for hermetical sealing, and it was then left at 25° C. for 5 minutes.
3. 1 g of the formulated second agent was applied to the tress wound around the rod. The rod was entirely covered with a plastic film for hermetical sealing, and it was then heated for 1 hour in an oven, which was set at 90° C.
4. The tress was removed from the oven, and cooled to a room temperature.
5. The tress was removed from the rod, and was then rinsed with running tap water at 30° C. for 30 seconds. Thereafter, a shampoo for evaluation was lathered on the tress for 60 seconds.
6. The tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking.
7. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.

(Evaluation Criteria for the Effect of Giving Initial Shape to Hair)

A: The curl diameter is 1 time or more and less than 2 times as large as the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has been maintained, and the hair shape has not changed from before the treatment.

<II: Imparting a Semi-Permanent Straight Shape to Semi-Permanent Curly-Shaped Hair>

1. The tress, which had been evaluated in <I: Imparting a semi-permanent curly shape> above, was combed to detangle it, and a flat iron with an actual temperature of 180° C. was then slid through the tress at a rate of 5 cm/sec six times.
2. The tress was rinsed with running tap water at 30° C. for 30 seconds, and a shampoo for evaluation was then lathered on the tress for 60 seconds. Thereafter, the tress was rinsed with running tap water at 30° C. for 30 seconds, and was then dried with a towel.
3. The tress was dried, while being shaken, so that the natural shape of hair could appear (wherein dryer was not used), and it was then combed. Thereafter, the tress was hung, and was then visually observed from the side.

(Evaluation Criteria for the Effect of Giving Shape to Hair Again)

A: The curl has not remained, and the hair is completely deformed into straight hair.
B: The curl has become weaker than before the treatment with a flat iron, but the hair has not been completely deformed into straight hair.
C: The curly hair has been maintained, and the hair shape has not changed from before the treatment.

<III: Imparting a Semi-Permanent Curly Shape to Semi-Permanent Straight-Shaped Hair>

1. The tress, which had been evaluated in <II: Imparting a semi-permanent straight shape to semi-permanent curly-shaped hair> above, was wetted with tap water at 30° C. for 30 seconds, and the wet tress was then wound around a plastic rod with a diameter of 14 mm, and fixed with a clip.
2. The rod was entirely covered with a plastic film for hermetical sealing. Thereafter, the tress was heated in an oven, which was set at 40° C., for 1 hour.
3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking.
6. The tress was hung and allowed to stand a laboratory for 2 hours, to be dried. The tress was combed, was then hung, and was then photographed from the side. Based on the photograph, the radius of curvature of the strongest curly portion in the tress was measured. The obtained value was doubled to obtain a curl diameter.

(Evaluation Criteria for the Effect of Giving Shape to Hair Once More)

A: The curl diameter is 1 time or more and less than 2 times as large as the used rod (diameter: 14 mm)
B: The curl diameter is 2 times or more and less than 3 times as large as the used rod (diameter: 14 mm)
C: The curl diameter is 3 times or more and less than 4 times as large as the used rod (diameter: 14 mm)
D: The curl diameter is 4 times or more and less than 50 times as large as the used rod (diameter: 14 mm)
E: Straight hair has been maintained, and the hair shape has not changed from before the treatment.

TABLE 4

|  |  |  |  | Example 16 |
|---|---|---|---|---|
| Formulated first agent | Formulation [mass %] | (A) Others (C) | Glyoxylic acid Sodium hydroxide Deionized water | 20 (*1) Balance |
|  |  |  | Total | 100 |
|  |  |  | pH | 2 |
| Formulated second agent | Formulation [mass %] | (B) Others (C) | Resorcinol Sodium hydroxide Deionized water | 30 (*1) Balance |
|  |  |  | Total | 100 |
|  |  |  | pH | 2 |
| Component molar ratio |  |  | (B)/(A) | 1 |
| Evaluation results |  |  | I. Imparting a semi-permanent curly shape | D |
|  |  |  | II. Imparting a semi-permanent straight shape to semi-permanent curly-shaped hair | A |
|  |  |  | III. Imparting a semi-permanent curly shape to semi-permanent straight-shaped hair | D |

*(1): Amount for adjusting to pH 2.0

Example 17

The same formulated first agent and formulated second agent as those used in Example 16 were used, and evaluation was carried out by the same procedures as those in Example 16, with the exception that the order of applying these parts was changed. Specifically, in the evaluation of <I: Imparting a semi-permanent curly shape> above, 1 g of the formulated second agent was first applied to the tress, which had been wound around a rod. The rod was entirely covered with a plastic film, and it was then left at 25° C. for 5 minutes. Thereafter, 1 g of the formulated first agent was applied to the resulting tress, and the rod was entirely covered with a plastic film for hermetically sealing. The tress was heated for 1 hour in an oven, which was set at 90° C. Other than these conditions, the same procedures as those described in Example 16 were carried out.

The treated tress was observed. As a result, the evaluation for <I: Imparting a semi-permanent curly shape> was C, the evaluation for <II: Imparting a semi-permanent straight shape to semi-permanent curly-shaped hair> was A, and the evaluation for <III: Imparting a semi-permanent curly shape to semi-permanent straight-shaped hair> was C.

Comparative Example 7

In accordance with Patent Document 3 (U.S. Pat. No. 4,278,659), a hair treatment agent was prepared, and <I: Imparting a semi-permanent curly shape> was then evaluated. Specifically, a hair treatment agent was prepared by the following procedures, and it was then evaluated.
<Preparation of Hair Treatment Agent>
An aqueous solution having pH 2.0, which comprised 5 mass % glyceraldehyde and 5 mass % resorcinol, was prepared. This aqueous solution was heated to reflux for 1 hour to obtain a hair treatment agent.
<I: Imparting a Semi-Permanent Curly Shape>
1. A 25 cm-long tress, which consisted of 0.5 g of Caucasian straight hair, was wetted with tap water at 30° C. for 30 seconds, and the wet tress was then wound around a plastic rod with a diameter of 14 mm, and fixed with a clip.
2. 1 g of the treatment agent prepared in <Preparation of hair treatment agent> above was applied to the tress wound around the rod. The rod was entirely covered with a plastic film for hermetical sealing, and was then heated for 1 hour in an oven, which was set at 90° C.
3. The tress was removed from the oven, and cooled to a room temperature.
4. The tress was removed from the rod, and was then rinsed with running tap water at 30° C. for 30 seconds. Thereafter, a shampoo for evaluation was lathered on the tress for 60 seconds.
5. The tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking.
6. The tress was hung and allowed to stand a laboratory for 2 hours, to be dried. The tress was combed, was then hung, and was then photographed from the side.

The hair treatment was carried out by the above described procedures. After hair had been treated with the hair treatment agent used in Comparative Example 7, it had the same hair shape as that of untreated hair, and thus, this hair treatment agent could not provide a curly shape to the hair.

Method Example 1

The following operations (I and II) were carried out.
<I: Imparting a Semi-Permanent Curly Shape>
A 25 cm-long tress, which consisted of 0.5 g of Caucasian straight hair, was wetted with tap water at 30° C. for 30 seconds, and the wet tress was then wound around a plastic rod with a diameter of 14 mm, and fixed with a clip.
0.5 g of an aqueous solution of 20 mass % glyoxylic acid (pH=2.0) was applied to the tress wound around the rod, and it was then allowed to stand at 25° C. for 5 minutes. Thereafter, 0.5 g of an aqueous solution of 30 mass % resorcin (pH=2.0) was applied to the tress, and the rod was entirely covered with a plastic film for hermetical sealing. After that, the tress was heated for 1 hour in an oven, which was set at 90° C.

The tress was removed from the oven, and cooled to a room temperature. The tress was removed from the rod, and was then rinsed with running tap water at 30° C. for 30 seconds. Thereafter, a shampoo for evaluation was lathered on the tress for 60 seconds. The tress was rinsed with running tap water at 30° C. for 30 seconds, and immersed at an infinite bath ratio in tap water at 30° C. for 60 seconds.

Thereafter, the tress was gently pulled up out of the water while the root thereof was held, and water was then drained off by light shaking. Thereafter, the tress was hung and allowed to stand a laboratory for 2 hours, to be dried. Subsequently, the tress was combed, was then hung, and was then visually observed from the side. As a result, it was found that a semi-permanent curly shape was provided to the tress.

<II: Imparting a Semi-Permanent Straight Shape to Semi-Permanent Curly-Shaped Hair>

The tress, which had been evaluated in <I: Imparting a semi-permanent curly shape> above, was combed to detangle it, and a flat iron with an actual temperature of 140° C. was slid through the tress at a rate of 5 cm/sec six times. Thereafter, the tress was rinsed with running tap water at 30° C. for 30 seconds, and a shampoo for evaluation was then lathered on the tress for 60 seconds. Thereafter, the tress was rinsed with running tap water at 30° C. for 30 seconds, and was then dried with a towel. The tress was dried, while being shaken, so that the natural shape of hair could appear, and it was then combed. Thereafter, the tress was hung, and was then visually observed from the side. As a result, it was found that a semi-permanent straight shape was provided to the tress.

Method Example 2

The following operations (I and II) were carried out.
<I: Imparting a semi-permanent curly shape>

A 25 cm-long tress, which consisted of 0.5 g of Caucasian straight hair, was wetted with tap water at 30° C. for 30 seconds, and the wet tress was then wound around a plastic rod with a diameter of 14 mm, and fixed with a clip.

0.5 g of an aqueous solution of 30 mass % resorcin (pH=2.0) was applied to the tress wound around the rod, and it was then allowed to stand at 25° C. for 5 minutes. Thereafter, 0.5 g of an aqueous solution of 20 mass % glyoxylic acid (pH=2.0) was applied to the tress, and the rod was entirely covered with a plastic film for hermetical sealing. After that, the tress was heated for 1 hour in an oven, which was set at 90° C.

The tress was removed from the oven, and cooled to a room temperature. The tress was removed from the rod, and was then rinsed with running tap water at 30° C. for 30 seconds. Thereafter, a shampoo for evaluation was lathered on the tress for 60 seconds. After that, the tress was rinsed with running tap water at 30° C. for 30 seconds, and immersed at an infinite bath ratio in tap water at 30° C. for 60 seconds. Thereafter, the tress was gently pulled up out of the water while the root thereof was held, and water was then drained off by light shaking. The tress was hung and allowed to stand a laboratory for 2 hours, to be dried. Subsequently, the tress was combed, was then hung, and was then visually observed from the side. As a result, it was found that a semi-permanent curly shape was provided to the tress.

<II: Imparting a Semi-Permanent Straight Shape to Semi-Permanent Curly-Shaped Hair>

The tress, which had been evaluated in <I: Imparting a semi-permanent curly shape> above, was combed to detangle it, and a flat iron with an actual temperature of 140° C. was slid through the tress at a rate of 5 cm/sec six times. Thereafter, the tress was rinsed with running tap water at 30° C. for 30 seconds, and a shampoo for evaluation was then lathered on the tress for 60 seconds. After that, the tress was rinsed with running tap water at 30° C. for 30 seconds, and was then dried with a towel. The tress was dried, while being shaken, so that the natural shape of hair could appear, and it was then combed. Thereafter, the tress was hung, and was then visually observed from the side. As a result, it was found that a semi-permanent straight shape was provided to the tress.

Method Example 3

The following operations (STEPS 1 to 3) are carried out.
<STEP 1: Imparting a Semi-Permanent Straight Shape>

An aqueous solution of 20 mass % glyoxylic acid (pH=2.0) is mixed with an aqueous solution of 30 mass % resorcin (pH=2.0) at a mixing ratio of 1:1, to prepare a treatment agent A. A 25 cm-long tress, which consists of 0.5 g of Caucasian curly hair, is wetted with tap water at 30° C. for 30 seconds. Thereafter, 1 g of the treatment agent A is applied to the tress. The tress is entirely covered with a plastic film for hermetical sealing, and is then heated for 1 hour in an oven, which is set at 40° C.

The tress is removed from the oven, and cooled to a room temperature. The plastic film is removed, and an excessive treatment agent is removed from the hair with a towel. Thereafter, the hair is dried with a dryer, while being combed.

After completion of the drying with a dryer, using a flat iron (Taiff Titanium, manufactured by Daihatsu) with a preset temperature of 230° C., the root side of the tress is held with the plates of the flat iron, and an operation to slide the flat iron from the roots to the tips of the tress at a rate of 5 cm/sec, while the hair is held with the plates, is carried out six times.

After completion of the iron treatment, the tress is rinsed with running tap water at 30° C. for 30 seconds, and a shampoo for evaluation is then lathered on the tress for 60 seconds. Thereafter, the tress is rinsed with running tap water at 30° C. for 30 seconds, is then dried with a towel, and is then naturally dried. As a result, a semi-permanent straight shape is provided to the resulting tress.

<STEP 2: Imparting a Semi-Permanent Curly Shape>

The tress, which has been evaluated in STEP 1 above, is wetted with tap water at 30° C. for 30 seconds, and the wet tress is then wound around a plastic rod with a diameter of 14 mm, and fixed with a clip. The rod is entirely covered with a plastic film for hermetical sealing, and the tress is then heated for 1 hour in an oven, which is set at 40° C. Thereafter the tress is removed from the oven, and cooled to a room temperature. The tress is removed from the rod, and is then rinsed with running tap water at 30° C. for 30 seconds. Thereafter, a shampoo for evaluation is then lathered on the tress for 60 seconds. The tress is rinsed with running tap water at 30° C. for 30 seconds, and immersed at an infinite bath ratio in tap water at 30° C. for 60 seconds. Thereafter, the tress is gently pulled up out of the water while the root of the tress is held, and water is then drained off by light shaking. The tress is hung and allowed to stand in a laboratory for 2 hours, and is allowed to stand, and dried. The tress is combed, is then hung, and is then visually observed from the side. As a result, a semi-permanent curly shape is provided to the tress.

<STEP 3: Imparting a Semi-Permanent Straight Shape>

The tress, which has been evaluated in STEP 2 above, is combed to detangle it, and an iron with an actual temperature of 180° C. is slid through the tress at a rate of 5 cm/sec six times. The tress is rinsed with running tap water at 30° C. for 30 seconds, and a shampoo for evaluation is then lathered on the tress for 60 seconds. Thereafter, the tress is rinsed with running tap water at 30° C. for 30 seconds, and is then dried with a towel. The tress is dried, while being shaken, so that the natural shape of hair can appear, and it is then combed. Thereafter, the tress is hung, and is then visually observed. As a result, a semi-permanent straight shape is provided to the tress.

The invention claimed is:

1. A method of hair treatment for semi-permanently or permanently deforming the shape of hair, which comprises the following steps (i) and (ii):
   (i) applying an agent for hair deforming treatment, and then allowing the agent to permeate into the hair, wherein the agent for hair deforming treatment comprises the following components:
   (A) glyoxylic acid, or a hydrate or a salt thereof,
   (B) resorcin,
   (C) water, and
   (D) 4-Phenylethyl resorcin; wherein the agent for hair deforming treatment has a pH of 4 or less; wherein the molar ratio of the content of the component (B) to the content of the component (A), (B)/(A), is 0.2 or more and 5 or less, wherein the molar ratio of the content of the component (D) to the content of the component (B) is 0.1 or more and 2 or less; and
   (ii) heating and shaping the hair into which the agent for hair deforming treatment has permeated, wherein the heating temperature in the step (ii) is 50° C. or higher and 250° C. or lower; wherein the method does not comprise a step of applying a hair treatment agent comprising a reducing agent or a strongly-alkaline hair treatment agent having pH 12 to 14 to the hair.

2. The method of hair treatment according to claim 1, which comprises a step of wetting hair before the step (i).

3. The method of hair treatment according to claim 1, wherein the step (ii) is carried out under an environment in which evaporation of water is suppressed.

4. The method of hair treatment according to claim 3, wherein the evaporation of water is suppressed is by covering the hair or continuously spraying the hair with vapor.

* * * * *